United States Patent
Salah et al.

(10) Patent No.: US 11,666,418 B2
(45) Date of Patent: Jun. 6, 2023

(54) DENTITION CONTROL METHOD

(71) Applicant: DENTAL MONITORING, Paris (FR)

(72) Inventors: Philippe Salah, Paris (FR); William Ayache, Neuilly-sur-Seine (FR); Guillaume Ghyselinck, Cantin (FR); Laurent Debraux, Paris (FR); Thomas Pellissard, Clichy (FR)

(73) Assignee: DENTAL MONITORING, Paris (FR)

( * ) Notice: Subject to any disclaimer, the term of this patent is extended or adjusted under 35 U.S.C. 154(b) by 1212 days.

(21) Appl. No.: 16/094,245

(22) PCT Filed: Apr. 21, 2017

(86) PCT No.: PCT/EP2017/059555
§ 371 (c)(1),
(2) Date: Oct. 17, 2018

(87) PCT Pub. No.: WO2017/182654
PCT Pub. Date: Oct. 26, 2017

(65) Prior Publication Data
US 2019/0125493 A1    May 2, 2019

(30) Foreign Application Priority Data
Apr. 22, 2016 (FR) ...................... 1653595

(51) Int. Cl.
*A61C 7/08* (2006.01)
*A61C 7/00* (2006.01)
(Continued)

(52) U.S. Cl.
CPC ............... *A61C 7/08* (2013.01); *A61C 7/002* (2013.01); *A61C 9/0053* (2013.01); *G06T 7/254* (2017.01);
(Continued)

(58) Field of Classification Search
CPC ......... A61C 7/002; A61C 7/08; A61C 9/0053; G16H 30/40
See application file for complete search history.

(56) References Cited

U.S. PATENT DOCUMENTS 5,768,413 A * 6/1998 Levin ........................ G06T 7/12
382/173
10,248,883 B2 * 4/2019 Borovinskih ......... G06T 7/0014
(Continued)

FOREIGN PATENT DOCUMENTS

WO    2006065955 A2    6/2006
WO    2008149221 A1    12/2008
(Continued)

OTHER PUBLICATIONS

Machine Translation of WO 2016/066651, Saleh et al. 25 pages.*
Corresponding International Application, Application No. PCT/EP2017/059555, Search Report, dated Jul. 11, 2017, 10 Pgs.

*Primary Examiner* — Edward Moran
*Assistant Examiner* — Matthew P Saunders
(74) *Attorney, Agent, or Firm* — Ronald M. Kachmarik; Cooper Legal Group LLC

(57) ABSTRACT

A method for adjusting/monitoring an orthodontic appliance worn by a patient. Creating a numerical three-dimensional reference model of at least a part of a patient's arch. Creating a numerical three-dimensional reference model of the teeth of the at least a part of the patient's arch. Acquiring at least one updated image, under actual acquisition conditions, and searching, by deformation of the initial reference model, for an updated reference model corresponding to the positioning of the teeth during the acquisition of the updated image. Determining, depending a comparison model corresponding to an anticipated positioning of the teeth, a comparison model. Comparing the updated reference model with the comparison model. If comparison leads to an unsatisfactory (Continued)

result, creation of a replacement orthodontic appliance, by modification of the orthodontic appliance worn or by creation of a new orthodontic appliance, the replacement orthodontic appliance being configured accordingly.

27 Claims, 8 Drawing Sheets

(51) Int. Cl.
| | |
|---|---|
| *G16H 50/70* | (2018.01) |
| *G16H 30/40* | (2018.01) |
| *G16H 15/00* | (2018.01) |
| *G16H 50/50* | (2018.01) |
| *G16H 30/20* | (2018.01) |
| *G16H 50/20* | (2018.01) |
| *G06T 7/254* | (2017.01) |
| *A61C 9/00* | (2006.01) |
| *G06T 17/00* | (2006.01) |

(52) U.S. Cl.
CPC ............ *G06T 17/00* (2013.01); *G16H 15/00* (2018.01); *G16H 30/20* (2018.01); *G16H 30/40* (2018.01); *G16H 50/20* (2018.01); *G16H 50/50* (2018.01); *G16H 50/70* (2018.01); *G06T 2207/10028* (2013.01); *G06T 2207/30036* (2013.01); *G06T 2210/41* (2013.01)

(56) References Cited

U.S. PATENT DOCUMENTS

| | | | |
|---|---|---|---|
| 10,342,645 B2* | 7/2019 | Salah | A61B 5/064 |
| 10,966,667 B2* | 4/2021 | Salah | G06T 17/00 |
| 2008/0306724 A1* | 12/2008 | Kitching | A61C 7/00 704/2 |
| 2009/0191503 A1 | 7/2009 | Matov et al. | |
| 2009/0291417 A1 | 11/2009 | Rubbert et al. | |
| 2012/0288818 A1* | 11/2012 | Vendittelli | A61C 7/00 433/24 |
| 2017/0049311 A1* | 2/2017 | Borovinskih | A61C 7/002 |
| 2017/0100214 A1* | 4/2017 | Wen | G16H 30/20 |
| 2017/0296303 A1* | 10/2017 | Tod | G16H 10/20 |
| 2018/0344430 A1* | 12/2018 | Salah | G16H 20/30 |

FOREIGN PATENT DOCUMENTS

| | | | | |
|---|---|---|---|---|
| WO | WO-2008149221 A1 * | 12/2008 | | A61C 7/00 |
| WO | 2016066637 A1 | 5/2016 | | |
| WO | 2016066642 A1 | 5/2016 | | |
| WO | 2016066654 A1 | 5/2016 | | |
| WO | WO 2016/066651 A1 * | 5/2016 | | |

* cited by examiner

DENTITION CONTROL METHOD

TECHNICAL FIELD

The present invention concerns a method for checking the positioning and/or the shape and/or the appearance of a patient's teeth and a computer program for implementing this method. The invention also concerns a method for adjusting an orthodontic appliance worn by a patient.

STATE OF THE ART

It is desirable for everyone to regularly have their teeth checked, especially to verify that the position and/or shape and/or appearance of their teeth does not evolve unfavorably.

During an orthodontic treatment, this unfavorable evolution may lead, in particular, to modifying the treatment. After an orthodontic treatment, this unfavorable evolution, called "relapse", may lead to a repeat treatment. Finally, more generally and independently of any treatment, everyone may wish to monitor any movement and/or change in shape and/or appearance of their teeth.

Conventionally, checkups are done by an orthodontist or a dentist who are the only ones with suitable equipment available. These checkups are therefore expensive. Moreover, the visits are an imposition.

US 2009/0291417 describes a process permitting creating, then modifying three-dimensional models, especially for creating orthodontic appliances.

One objective of the present invention is to respond, at least partially, to above-mentioned problems.

SUMMARY OF THE INVENTION

The invention provides a method for checking the positioning and/or the shape of a patient's teeth, said method including the following steps:
a) Creating a numerical three-dimensional reference model of at least a part of a patient's arch, preferably at least one arch, or "initial reference model" and, preferably, for each tooth, defining from the initial reference model, a numerical three-dimensional model of said tooth, or "tooth model";
b) Acquiring at least one two-dimensional image of the patient's arches, called "updated image", under actual acquisition conditions;
c) Analyzing each updated image and creating, for each updated image, an updated map relating to a discriminant information;
d) Optionally, determining, for each updated image, virtual acquisition conditions roughly approximating said actual acquisition conditions;
e) Searching, for each updated image, for an updated reference model corresponding to the positioning and/or shape of the teeth when the updated image is acquired, the search preferably being done by means of a metaheuristic method, preferably an evolutionary method, preferably by simulated annealing, and
f) For each tooth model, comparing the positioning of said tooth model in the initial reference model and in the reference model obtained from the preceding steps, called "updated reference model", in order to determine the movement of the teeth between steps a) and b), and/or
comparing the shapes of the initial reference model and of the reference model obtained from the preceding steps, called "updated reference model", in order to determine the deformation and/or movement of teeth between steps a) and b).

As will be seen in more detail in the rest of the description, a method for checking the positioning and/or the shape of the teeth according to the invention makes it possible, from a simple image of the teeth, taken without precise pre-positioning of the teeth relative to the image acquisition device, for example a photograph taken by the patient, to accurately assess the movement and/or the deformation of the teeth since the initial reference model was created. This evaluation may be done, moreover, with a simple computer, a server or a mobile phone.

Preferably, step e) includes:
a first optimization operation making it possible to search for the virtual acquisition conditions best corresponding to the actual acquisition conditions in a reference model to test determined from the initial reference model, and
a second optimization operation making it possible to search, by testing a plurality of said reference models to test, for the reference model best corresponding to the positioning and/or shape of the patient's teeth when the updated image is acquired at step b).

Preferably, a first optimization operation is done for each test of a reference model to test during the second optimization operation.

Preferably, the first optimization operation and/or the second optimization operation, preferably the first optimization operation and the second optimization operation, implement a metaheuristic method, preferably an evolutionary method, preferably a simulated annealing.

Preferably, step e) includes the following steps:
e1) defining a reference model to test as being the initial reference model then,
e2) following the next steps, testing virtual acquisition conditions with the reference model to test in order to finely approximate said actual acquisition conditions;
 e21) determining virtual acquisition conditions to test;
 e22) creating a two-dimensional reference image of the reference model to test under said virtual acquisition conditions to test;
 e23) processing the reference image to create at least one reference map representing, at least partially, said discriminant information;
 e24) comparing the updated and reference maps so as to determine a value for a first evaluation function, said value for the first evaluation function depending on the differences between said updated and reference maps and corresponding to a decision to continue or to stop the search for virtual acquisition conditions approximating said actual acquisition conditions with more accuracy than said virtual acquisition conditions to test determined at the last occurrence of step e21);
 e25) if said value for the first evaluation function corresponds to a decision to continue said search, modification of the virtual acquisition conditions to test, then resumption at step e22);
e3) determining a value for a second evaluation function, said value for the second evaluation function depending on the differences between the updated and reference maps under the virtual acquisition conditions best approximating said actual acquisition conditions and resulting from the last occurrence of step e2), said value for the second evaluation function corresponding to a decision to continue or stop the search for a reference model approximating the shape and/or the positioning of the teeth during the acquisition of the updated image with more accuracy than said reference model to test used at the last occurrence of step e2), and if said value for the second evaluation function corresponds to a decision to continue said search, modification of the reference model to test by deformation of the reference model to test and/or by movement and/or by deformation of one or more tooth models, then resumption at step e2).

A method for checking the positioning and/or the shape of teeth according to the invention may also include one or more of the following optional characteristics:

at step a), an occlusal plane is determined according to the following operations:
  I. determining the points of the initial reference model that belong to one arch and that are at a distance from the other arch that is less than a predetermined distance, preferably at a distance of less than 3 mm from the other arch, called "contact points";
  II. optionally, filtering a part of the contact points, preferably so that the number of contact points belonging to the upper arch is identical to the number of contact points belonging to the lower arch, preferably by eliminating the points of one arch furthest from the other arch;
  III. linear regression, preferably by the least squares method, on all of the contact points remaining so as to determine the occlusal plane;

at step a), the following operations are conducted:
  i. projecting, into an occlusal plane, of contact points between the teeth of the patient's upper arch and lower arch, the contact points and/or the occlusal plane preferably being determined according to steps I to III;
  ii. determining the centroid of the projections of said contact points and creating a reference frame, in the occlusal plane, centered on said centroid;
  iii. determining, in said reference frame, the parabolic function having the highest coefficient of correlation with all of the projections of the contact points;
  iv. rotating all of the projections of the contact points around the centroid, and repeating the preceding operation iii until all of the projections of the contact points have run through a determined sector, preferably greater than 90°, greater than 180°, or even around 360°;
  v. identifying the highest coefficient of correlation for all of the angular positions of all of the projections of the contact points around the centroid, and the axis of the corresponding parabolic function;
  vi. determining a median longitudinal plane of the initial reference model, said plane passing through said axis and being perpendicular to the occlusal plane;

at step a), a tooth model is at least partially defined according to the following operations:
  i'. determining, at least partially, inner and outer gingival margins of the tooth arch concerned, preferably by analysis of the variations in the orientation of the surface of the initial reference model;
  ii'. projecting, into the occlusal plane, the inner and outer gingival margins;
  iii'. identifying deformations of the projections of the inner and outer gingival margins corresponding to the interdental regions, the vertices of these deformations being called "alignment point" (in an interdental region, the two projections each have a point, the two points pointing essentially toward each other, the end of a point being an alignment point);
  iv'. determining the shortest path, at the surface of the initial reference model, between two alignment points of inner and outer gingival margins, respectively, of an interdental region, preferably by a metaheuristic method, preferably evolutionary, preferably by simulated annealing, said shortest path defining, at least partially, a tooth model;

an updated image is acquired less than 7 days after step a then steps c) to are implemented from this updated image;

the time interval between steps a) and b) or between steps A and B may be more than 1 week, 2 weeks, 1 month, 2 months or 6 months;

at step b), a handheld acquisition device is used (and in particular, which is not immobilized, for example, by means of a stand resting on the ground) and/or the patient's head is not immobilized;

an individual device is used, chosen from the group consisting of a connected camera, a smart watch, a numerical tablet, a portable 3D scanner and a computer coupled with an image acquisition system, such as a webcam or a numerical camera, to implement step b) and preferably at least one of the steps, preferably all of the steps c) to f);

at step b), a retractor is used, having one, preferably more than two identification marks, preferably not aligned, and, preferably, the representation of the identification marks is used in the updated image for
  at step c) cropping the image and/or,
  at step d), roughly evaluating the actual acquisition conditions;

at step c), the discriminant information is chosen in the group made up of contour information, color information, density information, distance information, brightness information, saturation information, information regarding reflections and combinations of these pieces of information;

at step c), the discriminant information is an optimal discriminant information obtained using an optimization process according to the invention, described below;

at step d), the data provided by the acquisition device are used and, preferably, concerning its orientation;

at step e2), the virtual acquisition conditions sought comprise calibration parameters for the acquisition device implemented at step b);

an optimization is implemented by a metaheuristic method, preferably evolutionary, preferably by simulated annealing in order to:
  at step a), determine, at least partially, a gingival margin defining a tooth model, and/or
  at step e2), search for the virtual acquisition conditions corresponding to the actual acquisition conditions and/or
  at step e), search for a reference model corresponding to the updated image;

said metaheuristic method is chosen from the group made up of
  evolutionary algorithms, preferably chosen from:
    evolution strategies, genetic algorithms, differential evolution algorithms, distribution estimation algorithms, artificial immune systems, Shuffled Complex Evolution path recomposition, simulated annealing, ant colony algorithms, particle swarm optimization algorithms, tabu search, and the GRASP method;

kangaroo algorithms,

The Davidon-Fletcher-Powell method, the sound effects method, stochastic tunneling, random restart hill-climbing, the cross entropy method, and hybrid methods between the metaheuristic methods cited above;

from the comparison at step f), a map is produced showing the changes in the shape of the initial reference model and/or the movement of one or more tooth models;

the discriminant information used for the updated map and/or the reference map is, prior to this use, optimized by means of an optimization method according to the invention described below, comprising steps C1 to C3, the acquired image being the updated image or the reference image, respectively, and the reference model being the initial reference model or the reference model to test, respectively.

The invention also concerns the use of a method for checking the positioning of teeth according to the invention in order to detect a relapse, and/or determine an evolution rate of a change in the positioning of the teeth and/or optimize the orthodontist or dentist appointment date, and/or evaluate the efficacy of an orthodontic treatment, and/or evaluate the evolution of the tooth positioning towards a theoretical model corresponding to a determined positioning of the teeth, in particular an improved positioning of the teeth and/or in dentistry.

The method may especially be implemented during an orthodontic treatment, in particular to check the progress, step a) being implemented less than 3 months, less than 2 months, less than 1 month, less than 1 week, less than 2 days after the beginning of the treatment, i.e., after the installation of an appliance intended to correct the positioning of the patient's teeth, called "active retainer".

The method may also be implemented after an orthodontic treatment, to verify that the positioning of the teeth is not evolving unfavorably ("relapse"). Step a) is then preferably implemented less than 3 months, less than 2 months, less than 1 month, less than 1 week, less than 2 clays after the end of the treatment, i.e., after the installation of an appliance intended to maintain the positioning of the teeth, called "passive retainer".

In one embodiment, in order to exclusively check tooth movement, the tooth models are considered nondeformable in step e). In particular, at step e3), the reference model to test may only be modified by moving one or more tooth models.

The invention also concerns a method for adjusting an orthodontic appliance according to results obtained with said orthodontic appliance.

Conventionally, at the start of an orthodontic treatment, the orthodontist determines the position of the teeth that they want to obtain from the treatment, called "final setup". The final setup may be defined by using an impression or from a three-dimensional scan of the patient's teeth. Then the orthodontist creates a suitable orthodontic appliance for this treatment.

At regular intervals, the patient goes to the orthodontist for a visual checkup. Depending on their diagnosis, the orthodontist may modify the orthodontic appliance.

For example, if the orthodontic appliance is an appliance with a metal orthodontic archwire attached to the teeth, they may modify the tension exerted by the orthodontic archwire. If necessary, they may also have a new, better adjusted orthodontic appliance made.

The orthodontic appliance may be an aligner. An orthodontic aligner is conventionally presented in the form of a removable single-piece appliance, conventionally of a transparent polymer material, that has a molded trough so that several teeth of an arch, usually all the teeth of an arch, may be held there. The shape of the trough is designed to hold the aligner in position on the teeth, while exerting a corrective action on the position of some teeth.

Treatment with aligners is advantageously less restrictive for the patient. In particular, the number of orthodontist appointments is limited. Moreover, the pain is less than with a metal orthodontal archwire attached to the teeth.

The orthodontic aligner market is therefore growing.

If the orthodontic appliance is an aligner, conventionally, at the start of treatment, the shapes that the different aligners must have at different times during the treatment are determined, then all the corresponding aligners are created. At predetermined times, the patient changes aligner. Checkups may be done at regular intervals. If the orthodontist diagnoses a treatment maladaptation, they make a new impression of the teeth, or, equivalently, a new three-dimensional scan of the teeth, then order a new series of aligners. On average, it is estimated that the number of aligners finally created is around 45, instead of the 20 aligners conventionally planned at the start of the treatment.

WO2008/149221 describes a process making it possible to detect a drift in treatment. This drift may be measured by comparing numerical models of the patient's teeth. In the event of drift, the treatment may be recalculated. WI 2008/149221, however, does not suggest any solution making it possible to obtain a precise measurement of the drift without an orthodontist appointment.

The need to go to the orthodontist is an imposition for the patient. The patient's confidence in their orthodontist may also be undermined. Finally, this leads to additional costs.

The number of orthodontist checkups should therefore be limited.

One objective of the invention is to at least partially address this problem.

The invention proposes a method for adjusting an orthodontic appliance worn by a patient, the method including the following steps:

a') Creating an initial reference model of at least a part of a patient's arch, preferably at least one arch, preferably the two arches complying with step a);

b') Independently of steps a') and c'), but before step d'), creating a numerical three-dimensional reference model, called "objective reference model", corresponding to a desired positioning, at a time point of the treatment, particularly desired at the end of the treatment with said orthodontic appliance, of the teeth of said at least a part of said patient's arch;

c') Acquiring at least one updated image, under actual acquisition conditions, and searching, by deformation of the initial reference model, for an updated reference model corresponding to the positioning of the teeth during the acquisition of the updated image, the search being preferably carried out by means of a metaheuristic method, preferably an evolutionary method, preferably by simulated annealing, preferably complying with steps b) to e);

d') Determining, depending on the initial reference model and/or the objective reference model, a comparison model in which the teeth of the initial reference model are in an anticipated positioning, preferably such as essentially planned for the time point of the acquisition done at step c');

e') Comparing the updated reference model with the comparison model;

f') If, at step e'), said comparison leads to an unsatisfactory result, creation of a replacement orthodontic appliance, by modification of the orthodontic appliance worn or by creation of a new orthodontic appliance, the replacement orthodontic appliance being configured according to said result.

The replacement orthodontic appliance is designed according to the results of the comparison between an actual positioning of the teeth, evaluated by means of the updated reference model, and an anticipated positioning, corresponding to the comparison model. The replacement orthodontic appliance is configured at the time of the checkup cycle (steps c') to f)) and can therefore be well suited to the reality of the treatment.

Advantageously, the checkup cycle may be done remotely, from simple photographs taken by a mobile phone, so that the patient does not need to go anywhere in particular to the orthodontist. As will be seen in more detail in the remainder of the description, the creation of the updated reference model at step c') is actually possible without any special precautions, especially since the actual positioning of the teeth is measured with an updated reference model that results from a deformation of the initial reference model so that it corresponds to the observations provided by the updated images, i.e., so that the updated images are views of the deformed initial reference model.

The patient and/or the orthodontist may therefore easily evaluate the treatment, and, in particular, the efficacy of the orthodontic appliance worn by the patient, without needing to go to an orthodontist. Step c') may therefore be repeated as needed.

Moreover, it becomes possible, in practice, to only schedule an orthodontist appointment when the comparison of step e') leads to an unsatisfactory result and a replacement orthodontic appliance needs to be created.

Furthermore, the precision of the initial reference model allows an updated reference model to be obtained that is also very precise, without a new scan of the teeth being necessary. The tests done have shown that the updated images, and, in particular, the photographs taken at step c') are sufficient to determine, with precision, the deformation to apply to the initial reference model. The position of the teeth shown in the updated images determined by deformation of the initial reference model by analysis of the updated images corresponds with a very high precision to the measured reality.

To further improve this precision, preferably several updated images are used.

The updated reference model is advantageously exclusively determined from information relating to the patient independently of any statistical consideration on orthodontic treatments of third parties. The updated reference model is thus specific to the patient.

The invention is therefore based on the possibility of combining two sources of information of different natures, i.e., a precise initial reference model that provides no information on the movement of the teeth, and one or more updated images containing little information on the precise positioning of the teeth but whose analysis makes it possible, by means of the initial reference model, to determine with precision the movement of the teeth represented since the time point at which the initial reference model was created. Preferably, the deformation of the model is carried out by means of a metaheuristic method by which the updated image is compared with a succession of reference models obtained by deformation of the initial reference model, the model closest to the updated image, i.e., allowing an observation of said model corresponding to the updated image, being retained to constitute the updated reference model.

In the case of an orthodontic treatment by means of aligners, the method permits also limiting the number of aligners created. The aligners may, in particular, be created throughout the treatment, which enables them to be perfectly adjusted to the actual situation at the time that they need to be used.

Finally, the cost and duration of treatment are reduced.

The adjustment method may still include, in particular, one or more of the following optional characteristics:

the comparison model may be, in particular, the objective reference model or, preferably, a numerical three-dimensional model providing an estimation of the positioning, planned for an intermediate time point, of the teeth of the initial reference model, called "intermediate reference model";

preferably, the comparison model corresponds to a positioning of the teeth essentially anticipated for the time point of said acquisition. Preferably, an estimation of the positioning is provided, planned for an intermediate time point, of the teeth of the initial reference model, the duration between said intermediate time point and the time point of the acquisition done at step c') being less than 1 month, preferably less than 1 week, preferably less than 24 hours;

the process includes more than 2, more than 5, more than 10, even more than 20 checkup cycles, each checkup cycle being made up of an execution of steps c') to f);

at step d'), the comparison model is determined according to updated reference models determined during one or more checkup cycle steps c') prior to the checkup cycle comprising said step d'), in particular according to the updated reference model or models determined during the checkup cycle steps c') immediately preceding the checkup cycle comprising said step d');

at step c'), said updated image is acquired by means of the patient's telephone, the updated reference model is preferably sought by means of said telephone, and the updated reference model is transmitted via said telephone to an orthodontist;

before each scheduled date for a step c'), preferably less than 3 weeks, preferably less than 2 weeks, preferably less than one week before said date, a reminder message is sent to the patient, preferably on their telephone, so that they may do said step c');

steps c') to e') of each checkup cycle are done "remotely", i.e., without the patient going to the orthodontist;

at step d'), the comparison model is determined according to the parameter values of the orthodontic appliance worn;

at step e'), a report is established from said comparison providing diagnostic information and/or recommendations to modify the patient's treatment;

at step e')
a score is established from said comparison, called "updated", representing the treatment efficacy, and, preferably, said updated score is compared to a reference score representing the efficacy of an equivalent standard treatment and the patient is presented with the result of the comparison between the updated and reference scores;

at step f'), the tension of an orthodontic archwire of the orthodontic appliance worn is modified and/or an orthodontic archwire of the orthodontic appliance worn is switched out and/or an orthodontic aligner is created to replace the orthodontic appliance worn;

at step f'), a plurality of potential treatments for achieving a positioning of the teeth corresponding to the objective reference model is determined, said potential treatments are presented to the patient and/or to an orthodontist so that they may choose one of said potential treatments, and then said replacement orthodontic appliance corresponding to the chosen treatment is created;

at step f'), the patient determines if the result is unsatisfactory;

the orthodontic appliance worn is a first aligner, and the replacement orthodontic appliance is a second aligner, and, preferably, said second aligner is sent to the patient.

The invention also concerns a method for evaluating the behavior of an orthodontic appliance including implementing, in several iterations, an adjustment method according to the invention, with said orthodontic appliance and/or orthodontic appliances of the same type, for each occurrence of the adjustment method, data collection, said data including at least the initial reference model and/or the objective reference model, on the one hand, and one or more updated reference models, on the other hand, as well as parameter values of the orthodontic appliance worn by the patient during said occurrence, a statistical analysis of said data so as to establish a correlation between a parameter of the orthodontic appliance or appliances worn during said occurrences and the By making checkups easier, the adjustment method according to the invention allows a large amount of data on the action of orthodontic appliances to be collected. Advantageously, it makes statistical exploitation of these data possible.

The evaluation method of the behavior of an orthodontic appliance may still include, in particular, one or more of the following optional characteristics:

said adjustment method is implemented more than 10, preferably more than 100, preferably more than 1000, preferably more than 10,000, preferably more than 100,000 times, i.e. for a large number of patients;

after said statistical analysis, the results of said statistical analysis are used to optimize:
the design of an orthodontic appliance, and/or
the choice of an orthodontic appliance for a particular treatment and/or
the establishment of a diagnosis, and/or
the creation of a replacement orthodontic appliance, and/or the determination of a predictive model to create a comparison model.

The invention also concerns a method for monitoring the efficacy of an orthodontic appliance worn by a patient, the method including the following steps:

a") Creating an initial reference model of at least a part of an arch, preferably at least one arch, preferably the two arches of the patient complying with step a);

b") Acquiring at least one updated image, under actual acquisition conditions, and searching, by deformation of the initial reference model, for an updated reference model corresponding to the positioning of the teeth during the acquisition of the updated image, the search being preferably carried out by means of a metaheuristic method, preferably evolutionary, preferably by simulated annealing, preferably complying with steps b) to e);

c") determining, for at least one point of a tooth, the value of at least one positioning parameter in the updated reference model;

d") repeating the cycle of steps b") and c") and, at each cycle, graphic representation of said value of said positioning parameter so as to visualize the evolution over time of said value.

A positioning parameter is a useful parameter to determine the position or orientation of a tooth. For example, x, y and z are positioning parameters in an Oxyz Cartesian coordinate system. The radial coordinate, often denoted r or $\rho$, and called the radius, the angular coordinate, also called polar angle or azimuth, and often denoted t or $\theta$, and the height, often denoted h or z, are positioning parameters in a cylindrical reference frame. The values of these positioning parameters allow the position of a point in space to be defined.

A method for monitoring the efficacy of an orthodontic appliance allows the movement dynamics of at least one point of a tooth to be visualized. Preferably, this point is a noteworthy point, chosen to be representative of the intensity of action of the orthodontic appliance.

The point of the tooth is preferably the centroid of the tooth. It may also be, for example, the center of the vestibular face of the crown.

The positioning parameter is preferably chosen according to the desired action for the orthodontic appliance.

Graphic representation, preferably a curve, the time scale being preferably linear, permits immediately the dynamics of the action of the orthodontic appliance to be perceived. In particular, the observation that the curve increases or decreases less quickly as time passes, may be interpreted as meaning that the orthodontic appliance is losing its effectiveness.

Such a curve is particularly simple to understand, which makes it possible for patients themselves to use it.

In a preferred embodiment, the graphic representation includes indications on the satisfactory or unsatisfactory nature of said evolution. For example, the curve may change color if the slope is considered abnormal. Preferably, the curve may be displayed on an acquisition device, preferably a mobile phone, having been used for said acquisition. In particular, it may be viewable by the patient. Advantageously, the patient may therefore decide themselves, at the most opportune time, to take measures to modify or switch out their orthodontic appliance, for example, to make an appointment with the orthodontist.

The invention also concerns an electronic or paper document showing said graphical representation.

In one embodiment, the number of positioning parameters whose evolution is graphically shown is less than 10, preferably less than 5, preferably less than 4, preferably less than 3, preferably less than 2. In one embodiment, the number of points of the tooth whose evolution of one or more positioning parameters is graphically shown is less than 10, preferably less than 5, preferably less than 4, preferably less than 3, preferably less than 2. Decision making is facilitated.

Reducing the number of positioning parameters whose evolution is shown graphically and the number of points of the tooth, however, requires an appropriate choice of these parameters and these points of the tooth.

The invention also concerns the use of a method for checking the shape of teeth according to the invention in order to:
- visualize and/or measure and/or detect dental plaque, and/or an incipient cavity, and/or a microcrack, and/or wear, for example resulting from bruxism or the implementation of an orthodontic appliance, active or passive, notably in the event of breaking or detaching of an orthodontic archwire;
- visualize and/or measure and/or detect a change in volume, in particular during growth of the teeth or after a dental or orthodontic procedure, for example a deposit of adhesive on the surface of the teeth;
- evaluate the desirability of an interceptive treatment, before any orthodontic treatment, in particular to evaluate the benefit of an orthodontic treatment.

In one embodiment, to exclusively check the deformation of the teeth, in step e), the tooth models are considered to be fixed, i.e., are not moved between steps a) and b). In particular, at step e3), the reference model to test may only be modified by deformation of one or more tooth models.

The comparison of the shapes of the initial reference model and the updated reference model in order to determine the deformation of the teeth between steps a) and b) may, in particular, result from a comparison of the shape of one or more tooth models in the initial reference model and in the updated reference model.

The invention also concerns a method for checking the appearance property of a patient's teeth, said method including the following successive steps:
  A. acquisition, via a first acquisition device, of at least one first two-dimensional image of said teeth and a first reference gauge, called "initial image";
  B. acquisition, via a second acquisition device, of at least one second two-dimensional image of said teeth and a second reference gauge having the same appearance as the first reference gauge, called "updated image";
  C. normalization of the initial and updated images so that the representations of the first and second reference gauges in the normalized initial and updated images have the same appearance;
  D. before or after step C., identification of the same region of the teeth on the initial and updated images;
  E. comparison of the appearance of said region in the normalized initial and updated images.

A method for checking the appearance of teeth according to the invention preferably includes one or more of the following optional characteristics:
  the time interval between steps A. and B. is greater than one week;
  the first acquisition device and/or the second acquisition device are cameras and/or mobile phones;
  the acquisitions at steps A. and/or B. are done with a flash;
  the reference gauges used for each of steps A. and B. have the same appearance;
  the reference gauges used for each of steps A. and B. are fixed on a dental retractor;
  the acquisitions at step A. and/or B. are done using an acquisition kit according to the invention, described below;
  the reference gauges used for each of steps A. and B. are identification marks;
  the first acquisition device and/or the second acquisition device includes a computer program comprising program code instructions for locating, in real time, the identification mark or marks on the retractor, analyzing its or their positions and/or dimensions, in particular the relative positions of several identification marks and, consequently, providing information, preferably light or sound information, so as to inform the user of said acquisition device;
  at step D., the location comprises a comparison of discriminant information common to both initial and updated images, and then an identification of the position of said region with respect to said common discriminant information;
  at step D, the location of the region on the initial and/or updated images comprises a search for virtual acquisition conditions in which the first and/or second acquisition device, respectively, would have acquired said initial and/or updated image, respectively, by observing a numerical three-dimensional reference model of the patient's arches.
  at step D., the location of the region in the initial and/or updated images comprises the implementation of an evaluation method for the actual acquisition conditions according to the invention, described below.

The invention also concerns an acquisition kit, notably for the implementation of step b), A. or B., said acquisition kit including:
  a dental retractor intended to be placed in the mouth of a patient and having an identification mark;
  an image acquisition device having:
    a display screen,
    a computer memory containing information on the target acquisition conditions,
    a computer program comprising program code instructions to simultaneously display, on said screen, an acquirable image and a reference, said reference being in a position so that, when the identification mark corresponds to the reference on the screen, the acquisition device respects the target acquisition conditions.

An acquisition kit according to the invention may notably be implemented at step b) of a method for checking the positioning and/or the shape of the teeth according to the invention, or at steps A. and/or B. of a method for checking the appearance of the teeth, and more generally, any method including an evaluation of the acquisition conditions of an image.

As can be seen in more detail in the remaining description, an acquisition kit according to the invention permits, in particular, positioning the acquisition device in a position that corresponds essentially to a predetermined position, for example considered as optimal for the desired checkup. An acquisition kit according to the invention therefore permits considerably improving the speed of information processing or the implementation of the checkup methods according to the invention.

An acquisition kit according to the invention preferably has one or more of the following optional characteristics:
the acquisition device is a mobile phone;
the reference is chosen from the group made up of:
a point,
a geometric shape, preferably a circle, a square, a rectangle or a line,
a colored area of the same color as said identification mark,
an identical shape to the shape of said identification mark,
a complementary shape to the shape of said identification mark, in particular to make a shape having a meaning, such as a geometric shape, a letter or a text, drawing or a pattern, and
combinations thereof;
the retractor has several nonaligned and preferably coplanar identification marks;
the identification mark is arranged so that, when it corresponds to said reference on the screen, itis at least 1 cm from the edge of the screen.

The invention also concerns a method of acquiring a two-dimensional image of a part of a dental arch, or a dental arch or the two dental arches of a patient by means of an acquisition kit according to the invention, in particular for the implementation of a step b), A. and/or B. This method is noteworthy in that it includes the following successive steps:

(a) determining target acquisition conditions, for example according to a treatment to be applied, in particular, to an orthodontic treatment, and determining matching conditions adjusted to match up an identification mark of the retractor with a reference displayed on the screen of the acquisition device so that it results in the application of the target acquisition conditions;

(b) programming the acquisition device so as to display the reference a position so that said match results in the application of the target acquisition conditions;

(c) placing the retractor in the patient's mouth;

(d) positioning the acquisition device so as to match up the identification mark and the reference, as well as to apply the target acquisition conditions;

(e) acquiring the acquirable image in the positioning of the acquisition device adopted in the preceding step.

The target acquisition conditions are the conditions permitting a suitable positioning of the acquisition device, preferably an optimal positioning of the acquisition device to acquire the image. Preferably, the target acquisition conditions are therefore determined depending on the teeth to observe.

Preferably, an acquisition method according to the invention is implemented for the steps of the checkup methods according to the invention requiring the acquisition of a two-dimensional image of a part of a dental arch or one dental arch or the two dental arches of a patient, in particular for steps b).

Preferably, the cycle of steps (a) to (e) is repeated several times, preferably more than twice, even more than three times, with different target acquisition conditions.

For example, to measure the movement of a tooth, first target acquisition conditions may correspond to a positioning at 40 cm of the retractor, opposite and at the height of the retractor. Second and third target conditions may correspond to a positioning at 40 cm of the retractor, at the height of the retractor, at 45° to the right and left of the sagittal plane, respectively.

Preferably, steps (c), (d) and (e) are executed by a person without university training in orthodontics and/or outside any medical, dental or orthodontic practice, and/or without the use of a device for mechanical stabilization of the acquisition device and/or without the use of devices other than a mobile phone and/or without the use of a calibration gauge.

The invention also concerns a method of optimizing a discriminant information extracted from a two-dimensional image of the dental arches of a patient, called "acquired image", by means of a three-dimensional numerical reference model of at least a part of an arch of the patient, or one arch or the two arches of the patient, said method including the following steps:

C1. evaluating the quality of the discriminant information and of a quality limit, filtering so as to retain only the discriminant information presenting a quality higher than the quality limit, and definition of "discriminant information to test" as being the discriminant information retained;

C2. testing a concordance between the discriminant information to test and said reference model;

C3. evaluating the test result, and depending on said evaluation:
adding discriminant information not retained to the discriminant information to test and/or deletion of discriminant information in the discriminant information to test, then resumption at step C2. or,
defining optimal discriminant information as being the discriminant information to test.

Preferably, an optimization method according to the invention still has one or more of the following optional characteristics:

the discriminant information is chosen from the group made up of contour information, color information, density information, distance information, brightness information, saturation information, information regarding reflections and combinations of these pieces of information.

step C2. includes the following steps:
searching for virtual acquisition conditions approximating, preferably optimally, the actual acquisition conditions under which said acquired image has been acquired and observation of the reference model under said virtual acquisition conditions so as to obtain a reference image;
processing the image acquired and the reference image to create at least one acquired map and one reference map, respectively, said acquired and reference maps showing said discriminant information;
comparing the acquired and reference maps so as to determine a degree of concordance, the result of the test of dependent step C2., preferably being equal to said degree of concordance;

the search for virtual acquisition conditions approximating the actual acquisition conditions includes the following steps:
01) optionally, determining rough virtual acquisition conditions approximating said actual acquisition conditions, preferably by analyzing the representation, on the acquired image, of a retractor used during the acquisition of the acquired image;
02) determining virtual acquisition conditions to test;
03) creating a two-dimensional reference image of the reference model observed under the virtual acquisition conditions to test;
04) processing the reference image to create at least one reference map representing said discriminant information;
05) comparing the acquired and reference maps so as to determine a value for an evaluation function, said value for the evaluation function depending on the differences between said acquired and reference maps and corresponding to a decision to continue or to stop the search for virtual acquisition conditions approximating the actual acquisition conditions with more accuracy than said virtual acquisition conditions to test;
  if said value for the evaluation function corresponds to a decision to continue said search, modification of said virtual acquisition conditions to test, then resumption at step 03);
  otherwise, evaluating the actual acquisition conditions by said virtual acquisition conditions to test;
determining the discriminant information to add and/or to add at step C3. results from the implementation of a metaheuristic method, preferably an evolutionary method.

The invention also concerns an evaluation method for the actual acquisition conditions of a two-dimensional image of a patient's teeth, called "acquired image", said method including the following steps:
001) creating a digital three-dimensional reference model of at least a part of an arch, preferably one arch, preferably the two arches of the patient;
002) analyzing the image acquired and creating a map relating to a discriminant information, called "acquired map";
003) searching for virtual acquisition conditions approximating said actual acquisition conditions, preferably according to steps 01) to 05).

One or more possibly optional characteristics from step a) are applicable to step 001). In particular, the reference model may be prepared, by a scan, from measurements made on the patient's teeth or on a physical model of their teeth, for example a plaster model.

One or more possibly optional characteristics from step c) are applicable to step 002).

The invention also concerns:
a computer program, and in particular, a specialized application for a mobile phone, comprising program code instructions for the execution of one or more, preferably all of steps b) to f) or A. to E. or C1 to C3, when said program is executed by a computer,
a computer medium onto which such a program is recorded, for example a memory or a CD-ROM, and
a personal device, in particular a mobile phone or a tablet, onto which such program is loaded.

The invention also concerns a system including:
a three-dimensional scanner able to implement step a) of a method for checking the positioning and/or the shape of teeth according to the invention, or step 001),
a personal device, preferably a mobile phone, loaded with a program according to the invention.

DEFINITIONS

"Patient" means any person for whom a method is implemented in order to check the teeth, whether or not this person is sick, or whether or not this person is undergoing treatment.

"Dental healthcare professional" means a dentist, orthodontist or an orthodontic laboratory.

"Dentist" means a dentist or dental assistant working under the supervision of a dentist.

"Dentition" means both dental arches of the patient.

An image of an arch is, of course, a partial representation of this arch.

A "mobile phone" is a device of less than 500 g with a sensor allowing it to capture images, which may exchange data with another device more than 500 km from the mobile phone, and able to display said data, especially said images.

For a method for checking teeth positioning, the "acquisition conditions" specify the position and orientation in space of an image acquisition device relative to the patient's teeth or a model of the patient's teeth, and preferably the calibration of this image acquisition device.

The "calibration" of an acquisition device consists of all the calibration parameter values. A calibration parameter is a parameter intrinsic to the acquisition device (unlike its position and orientation) whose value influences the image acquired. For example, the aperture is a calibration parameter that modifies the depth of field. Exposure time is a calibration parameter that modifies the luminosity (or "exposure") of the image. The focal length is a calibration parameter that modifies the view angle, i.e., the degree of "zoom". "Sensitivity" is a calibration parameter that modifies the reaction of the sensor of a numerical acquisition device to incident light.

Preferably, the calibration parameters are chosen from the group made up of the aperture, exposure time, focal length and sensitivity.

The "occlusal plane" is the plane that provides the best linear correlation with all the contact points between the teeth of the upper arch, on the one hand, and the teeth of the lower arch, on the other hand.

The "median longitudinal plane" is the plane essentially vertical when the patient keeps their head straight, which essentially symmetrically separates the right and left parts of each arch.

A "tablet" is a portable touchscreen computer.

A 3D scanner is a device for obtaining a three-dimensional representation of an object.

"Image" means a two-dimensional image, such as a photograph. An image is formed of pixels.

A "preview" image is the image that the acquisition device can record at a given time point. For a camera or a telephone, it is the image that appears on the screen when the photo or video acquisition device is in operation.

A "discriminant information" is a characteristic piece of information that can be extracted from an image ("image feature"), conventionally by a computer processing of this image.

A discriminant information may have a variable number of values. For example, contour information may be equal to 1 or 0 depending on whether or not a pixel belongs to a contour. Brightness information may take on a large number of values. Image processing allows the discriminant information to be extracted and quantified.

Acquisition conditions are called "virtual" when they correspond to a simulation in which the acquisition device would be in said acquisition conditions (theoretical positioning and preferably calibration of the acquisition appliance).

"Comprising a" or "including a" or "having a", means "including at least one", unless otherwise indicated.

In the various methods described, the step references are identical if the steps are similar or identical.

BRIEF DESCRIPTION OF THE FIGURES

Other characteristics and advantages of the invention will appear upon reading the detailed description that follows and examining the attached drawing in which.

DETAILED DESCRIPTION OF A METHOD FOR CHECKING THE POSITIONING OF THE TEETH

A method for checking the positioning of teeth according to the invention includes the steps mentioned above.

Figure 1:
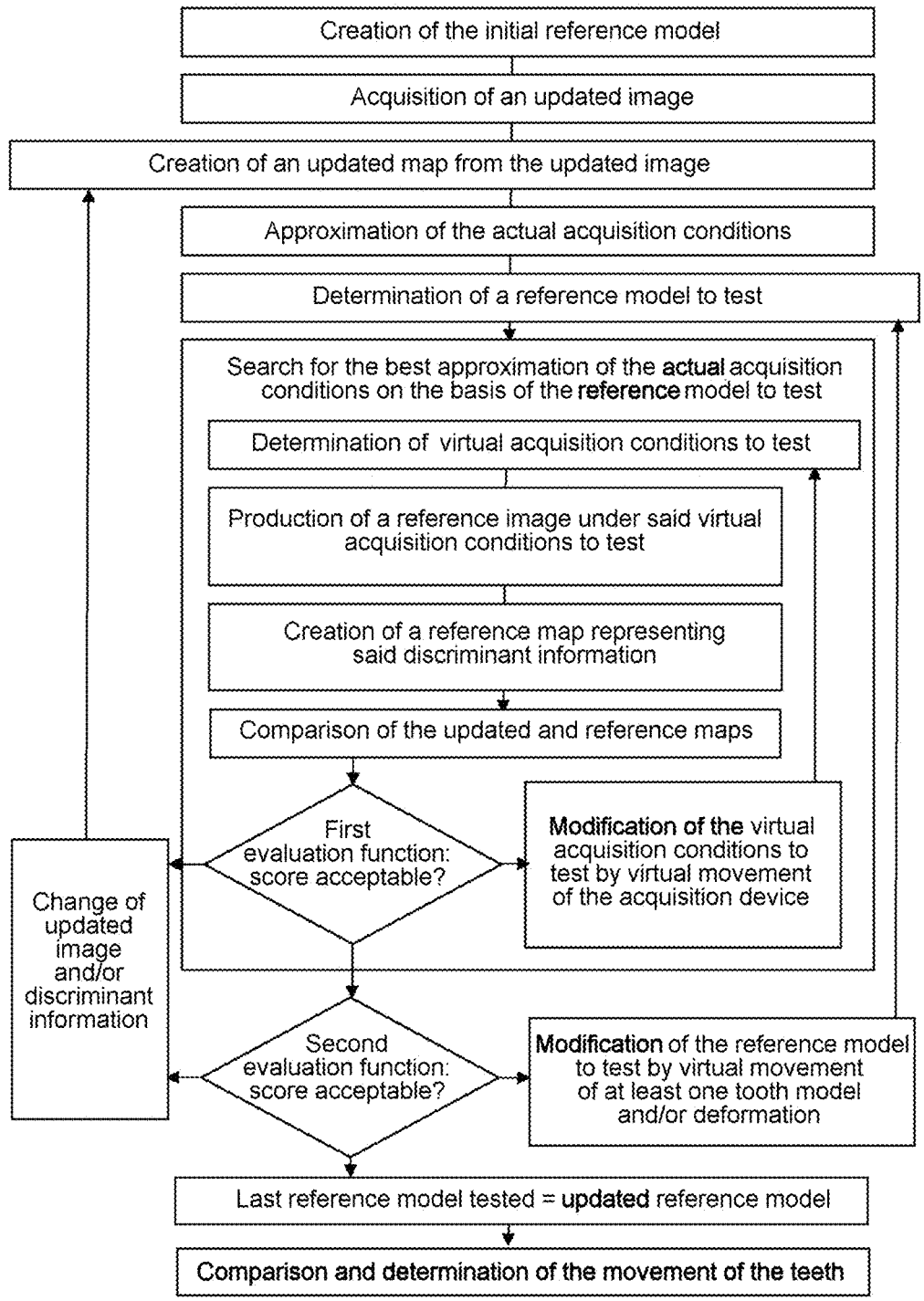
FIG. 1 is a flowchart illustrating the implementation of a method for checking the positioning and/or shape of the teeth according to the invention.
Figure 2:
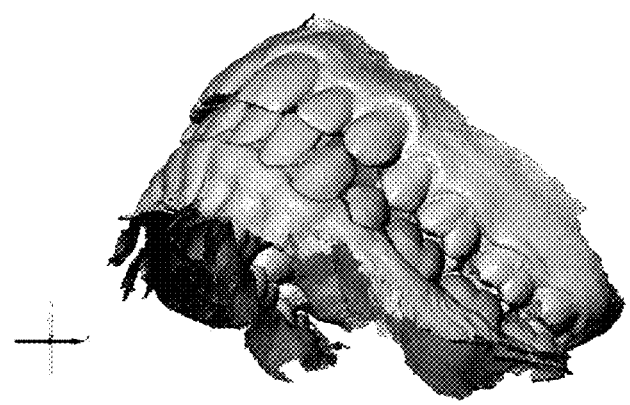
FIG. 2 shows one example of the initial reference model.

At step a), an initial reference model of the patient's arches, or a part of the patient's arches, is created (see FIG. 2).

The initial reference model is a numerical three-dimensional model of the patient's arches, for example of the .stl or .Obj, .DXF 3D, IGES, STEP, VDA, or Point cloud type.

Advantageously, such a model, called "3D", may be observed from any angle.

To monitor an orthodontic treatment, the initial reference model is preferably prepared at the start of treatment. The initial reference model may correspond to a positioning of the patient's teeth before the treatment or a positioning of the patient's teeth that the treatment proposes attaining. In this case, the initial reference model is conventionally calculated from a first three-dimensional model corresponding to the positioning of the patient's teeth before the treatment.

To check for relapse, the initial reference model is preferably prepared less than six months, preferably less than three months, more preferably less than one month after the end of the orthodontic treatment, generally immediately after the end of the treatment. It therefore corresponds to an essentially optimal positioning of the teeth.

The initial reference model may also be prepared independently of any treatment, for example because the patient wishes to monitor the movements of their teeth.

The initial reference model can be prepared from measurements made on the patient's teeth or on a physical model of their teeth, for example a plaster model.

The initial reference model is preferably created using a professional device, for example a 3D scanner, preferably implemented by a healthcare professional, for example an orthodontist or an orthodontic laboratory. In an orthodontic office, the patient or the physical model of their teeth may advantageously be positioned in a precise position and the professional device may be perfected. This results in a very precise initial reference model. The initial reference model preferably provides information on the tooth positioning with an error less than 5/10 mm, preferably less than 3/10 mm, preferably less than 1/10 mm.

Orientation of the Initial Reference Model

Preferably, the orientation of the initial reference model in space is determined, especially, preferably, the occlusal plane and the median longitudinal plane.

The occlusal plane and the median longitudinal plane may be determined manually, in an approximate manner. However, the inventors have discovered methods to determine these planes by computer processing.

Preferably, the reference model is a model of the arches with the mouth closed, i.e., in a position in which the teeth of the upper arch are in contact with the teeth of the lower arch.

Conventionally, the initial reference model provided by a three-dimensional scanner allows the upper arch to be distinguished from the lower arch. Generally, the model is provided in the form of two files respectively corresponding to these arches and including data for positioning the models of these arches with regard to one another in the occlusion position.

Preferably, in order to estimate the points of contact between the teeth of the upper and lower arches, all the points of the model of the upper and lower arches which are at a distance less than a predetermined limit are determined; this limit is preferably less than 3 mm, preferably about 2 mm. All other points of these models are then ignored, which leads to the representation of FIG. 3b. A linear regression then allows the occlusal plane ("plane 1" in FIG. 3c) to be determined.

Figure 3:
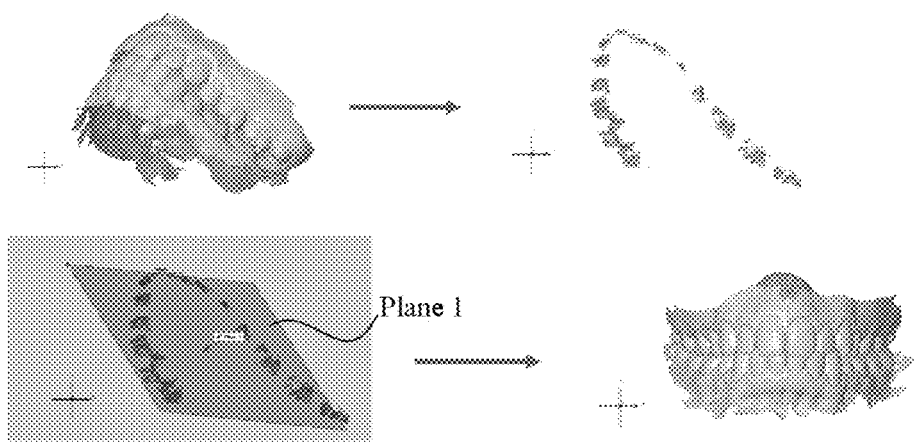
FIG. 3 illustrates the processing performed to determine the occlusal plane, FIG. 4 (4a-4d) illustrates the necessary step to determine the tooth models in a reference model, FIG. 5 (5a-5d) illustrates the acquisition of updated images, as well as the cropping operation, FIG. 6 (6a-6b) illustrates the processing of an updated image to determine the contour of the teeth, FIG. 7 schematically illustrates the relative position of identification marks 12 on updated images $14_1$ and $14_2$ of a retractor 10, along the direction of observation (dashed line)

The initial reference model can then be oriented along the occlusal plane (FIG. 3d).

If the initial reference model does not have data for positioning the upper and lower arches relative to each other, an occlusion bite is preferably used, showing the contact points between the upper teeth and the lower teeth, then the models of the upper and lower arches are repositioned in relation to this occlusion bite.

The median longitudinal plane is perpendicular occlusal plane, but its orientation is not known.

Preferably, the orientation of the median longitudinal plane is determined as follows:

Axes (Ox) and (Oy) are considered in the occlusal plane, point O being the centroid of the normal projections of die contact points on the occlusal plane.

In this reference (xOy), the curve is sought, preferably parabolic, having the greatest coefficient of correlation with all of said projections.

All of the projections of the contact points are then moved in the occlusal plane, by rotation around point O, and the previous step is repeated from this new angular position for the projections of the contact points.

The cycle of the previous operations is continued, preferably until all the points of contact have been rotated 360° around the centroid O. The coefficients of correlation corresponding to the different orientations of the set of contact points are then compared. The axis of the curve that leads to the highest coefficient of correlation is then considered to be included in the median longitudinal plane, which allows the orientation of this plane to be precisely defined.

The orientation in space of the initial reference model is therefore quickly perfectly determined.

Creating Tooth Models

Figures 4A, 4B:
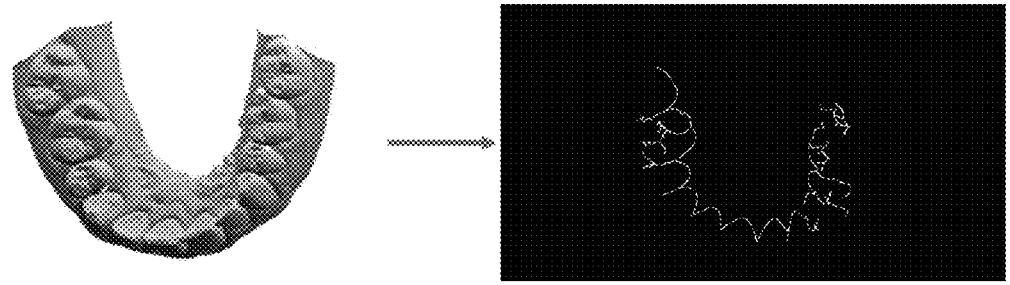

In the initial reference model, a part that corresponds to one tooth, or "tooth model" is defined by a gingival margin that may be broken down into an inner gingival margin (on the inside of the mouth relative to the tooth), an outer gingival margin (oriented toward the outside of the mouth relative to the tooth) and two lateral gingival margins. The gingival margins correspond to regions in which the orientation of the surface defined by the initial reference model undergoes high-amplitude modifications. These orientation variations may be identified according to known techniques, for example by identifying the changes of direction from the normal at the modelled surface. FIG. 4a represents a view of the initial reference model processed to show these changes of direction. FIG. 4b shows the inner gingival margin that can be extracted by analysis of the image of FIG. 4a.

Figure 4C:

Several views of the initial reference model are thus analyzed, which permits determining the inner and outer gingival margins in three dimensions, as shown in FIG. 4c.

Furthermore, by projection in the occlusal plane, the inner and outer gingival contours of an arch come closer to both sides of a tooth. To determine a lateral gingival margin of a tooth, the shortest path, on the surface of the initial reference model, is sought between the two points of the inner and outer gingival margins thus brought together and essentially facing each other. The search for the shortest path between two points on a three-dimensional model makes use of well-known optimization techniques. Preferably, this search results from a metaheuristic method, preferably evolutionary, preferably simulated annealing.

Figure 4D:
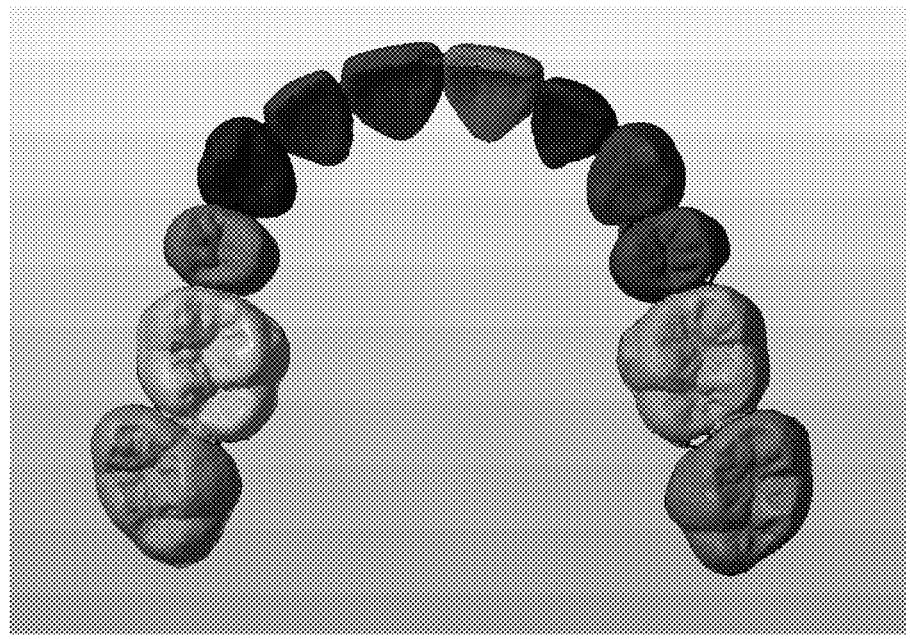

Two adjacent lateral gingival margins and the inner and outer parts of the gingival margins that connect these lateral gingival margins thus permit defining a tooth at the level of the gum. By considering that a tooth extends from the gingival contour to the occlusal plane, it is thus possible to determine the parts of the initial reference model that correspond to the different teeth ("tooth models"). FIG. 4d shows all the tooth models of an arch.

The initial reference model may be stored in a centralized database, grouping the initial reference models of a plurality of patients. This database may be physically installed in a specialized establishment. It may also be installed in an orthodontic laboratory or office, which limits transfer of confidential information.

In one embodiment, the initial reference model is given to the patient. Preferably, a computer file corresponding to the initial reference model is recorded on a removable medium, for example on a USB drive or on an electronic card, preferably on a mobile phone, a tablet or a laptop of the patient, and in particular on the personal device that will preferably be used at steps b) and beyond. Preferably, the patient or a dental healthcare professional loads the initial reference model onto said individual device or makes it available for loading onto said individual device. The patient preferably loads the initial reference model from the internet.

In one preferred embodiment, the reference model is not given to the patient. Preferably, the reference model is only made available at a specialized establishment to implement steps c) to f). it may remain stored in the establishment in which it was produced at step a) and where, preferably, steps c) to f) are implemented.

At step b), an updated image of a part of an arch, an arch, or the arches is taken by means of art image acquisition device. Step b) is preferably done by the patient or an associate of the patient, but may be done by a dentist.

Time of Acquisition

Preferably, the updated image is taken after a time interval $\Delta t$ after step a). The time interval $\Delta t$ may be predetermined. It may be constant, regardless of the occurrence of the method, that is to say that this interval relates to the first execution of the method or a subsequent execution. It may be variable, and depend, for example, on the results obtained following a previous execution of the method. In particular, for checking for relapse, the time interval $\Delta t$ may be all the shorter as this execution made it possible to detect a significant drift.

In a preferred embodiment, the time interval $\Delta t$ is determined by the orthodontist, according to a checkup schedule. Depending on the evolution of the position of the teeth, the orthodontist may modify this schedule and, consequently, modify the time interval $\Delta t$. In one embodiment, the method for checking the positioning of teeth according to the invention is executed several times, the time intervals between each execution being able to be identical or different. The time intervals between two successive executions may all be determined before the first execution to correspond to a checkup schedule created by the orthodontist.

The time interval $\Delta t$ may also be undetermined and depend, for example, on the patient's decisions. For example, an updated image may be created on the occasion of a dental appointment or any time that the patient wishes, even independently of any orthodontic treatment.

The time interval $\Delta t$ is preferably determined to correspond to a potentially significant evolution of the tooth positioning.

For example, to check for relapse, the time interval $\Delta t$ is preferably less than three months during the first year after treatment. After this first year, the time interval $\Delta t$ is preferably more than one month, even more than six months or more than 12 months. In particular, for detecting a tooth shift, a time interval comprised between six months and eighteen months is suitable.

Preferably, at least one reminder informing the patient of the need to create an updated image is sent to the patient. This reminder may be in the paper form or, preferably, in the electronic form, for example in the form of an email, a specialized mobile app automatic alert or an SMS. Such a reminder may be sent by the orthodontic office or laboratory or by the dentist or by the patient's specialized mobile app, for example.

In a preferred embodiment, an updated image is acquired before the teeth have been able to move significantly, essentially at the same time as the creation of the initial reference model, preferably less than 7 days, less than 3 days, less 1 day after step a), that is to say before the teeth have been able to move significantly. The implementation of the method with this updated image advantageously makes it possible to verify that the method does not lead to the detection of any difference between the initial and updated reference models, and therefore functions correctly.

In one embodiment, the updated image may be acquired before the creation of the initial reference model. For example, steps a) and b) may be done at the end and at the start of an orthodontic treatment, respectively. It is thus notably possible to evaluate the treatment efficacy in the absence of a 3D model at the start of treatment. The time interval $\Delta t'$ separating steps a) and b) in this embodiment may notably take the values described above for $\Delta t$.

Image Acquisition Device

Preferably, the image acquisition device is a personal device commonly commercially available, for example a mobile phone, a so-called "connected" camera, a so-called "smart" watch, or a tablet or personal computer, stationary or portable, having an image acquisition system, such as a webcam or a camera, preferably a numerical camera. Even though the updated image may, in particular, be created by a dentist, it is preferably created by the patient themselves, or one of their associates.

In particular, the updated image can be created by a person with no special knowledge of orthodontics, and in particular who has no degree in orthodontics or dentistry.

Preferably, the same acquisition device is used to take all the updated images.

The image acquisition device preferably weighs less than 3 kg, less than 2 kg, less than 1 kg, less than 500 g, preferably less than 300 g.

Step b) may therefore advantageously be carried out separately from step a), i.e., in a place different from that in which step a) is performed, in particular more than 50 m, more than 100 m, more than 1 km from the place where step a) is carried out, in particular, outside the orthodontic office. In one embodiment, step b) is not done in a dental office, an orthodontic office or an orthodontic laboratory, except, optionally, during a session intended to train the patient.

Preferably, the updated image is a photograph, in particular a panoramic photograph. In one embodiment, the updated image is extracted from a film.

In one preferred embodiment, the method uses several updated images to have at least one representation of each tooth, preferably at least three updated images corresponding to a front view, a right view and a left view of the patient's teeth.

Preferably, at step b), at least one updated image is taken in mouth-closed position and at least one updated image is taken in mouth-open position. The mouth-closed image advantageously allows the relative movements between the two arches to be identified. The updated mouth-open position advantageously allows the tooth contours to be clearly identified, without the teeth of the upper arch hiding the teeth of the lower arch, or vice versa.

Updated images may be taken either for the upper arch, or for the lower arch, or, preferably, for both arches, in all or in part.

Several similar images (essentially representing the same teeth) may also be useful to search for the best score. Depending on the acquisition conditions, a discriminant information may, in particular, lead to different scores depending on the updated image used.

Figure 5A:
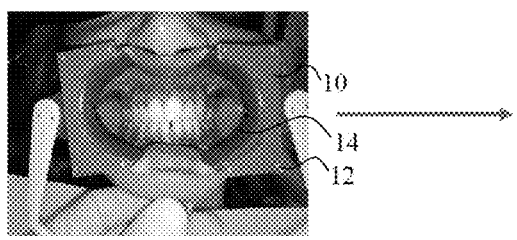
Figure 5B:
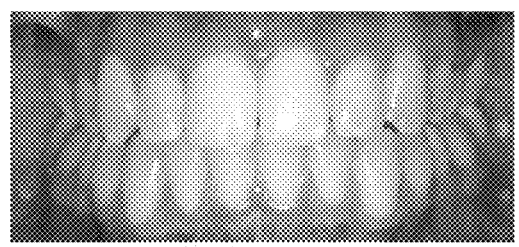
Figure 5C:
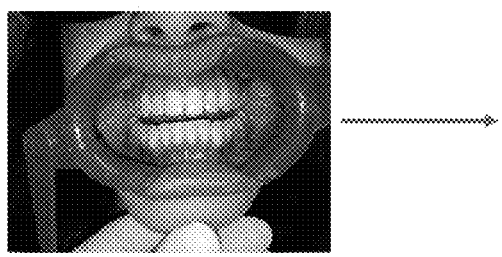
Figure 5D:
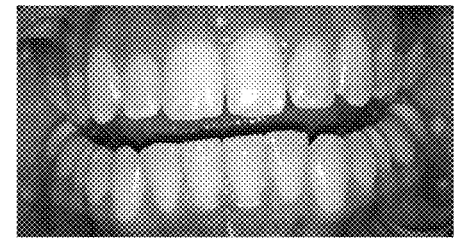

Preferably, a dental retractor is used in step b), as shown in FIGS. 5a and 5c. The first function of the retractor is to retract the lips to improve the visibility of the teeth. Preferably, a retractor is given to the patient, for example during an appointment with their orthodontist or dentist.

The image acquisition device preferably provides color images and/or infrared images of the patient's mouth, or even the patient's face. Color images preferably show the patient's mouth with the actual colors of this mouth. Infrared images advantageously permit showing the teeth with an excellent contrast.

Preferably, the image acquisition device includes a specialized app to implement step b), as well as, preferably, the subsequent steps, preferably all of the subsequent steps. More preferably, this app manages reminders and informs the patient of the need to create an updated image.

Preferably, the specialized app is loaded onto the image acquisition device from a physical medium such as a USB drive or a CD-ROM, or is downloaded from the Internet or via the airwaves. In one embodiment, the specialized app is provided to the patient by the orthodontic office and/or laboratory. In particular, it may take the form of an app of the type commonly downloaded on Apple® branded intones or devices of any brand implementing Android® operating systems or any other operating system.

The image acquisition device preferably includes a camera or a video camera or infrared camera, which the user, for example the patient or one of their associates, positions by means of a viewfinder or a screen, before activating it.

Foolproofing Means and Acquisition Kit

A method for checking the positioning of teeth according to the invention does not require precise positioning of the image acquisition device relative to the teeth.

In one embodiment, no positioning constraints ensuring an arrangement of the image acquisition device less than 30 cm, less than 20 cm, 10 cm or less than 5 cm from a determined location are imposed.

Preferably, the image acquisition device has foolproofing means, however, making its approximate positioning with regard to the patient easier before acquiring the updated image.

The user may be guided by written and/or vocal messages for acquisition. For example, the personal device may announce "take a photo from the front", sending a signal to inform the user that the photo is acceptable or that on the contrary, they must redo a photo, announce "take a photo on the right" preferably by displaying an arrow to orient the user, etc. The end of the acquisition process may also be announced by the device. The device may also assist in positioning, for example by visual messages (e.g., arrows) and/or audible messages (such as a succession of beeps whose frequency increases as the positioning of the device improves), and/or written and/or vocal messages ("higher", "lower", etc.).

The foolproofing means may, in particular, include references that appear on the viewfinder or screen. The references may for example include a line intended to be aligned with the general direction of the juncture between the upper teeth and the lower teeth when the teeth are clamped by the patient, and/or a vertical line intended to be aligned with the juncture between the two upper incisors. The references may also make reference to other parts of the patient. For example, they may be made up of marks corresponding to the position of the eyes or take the form of an outline in which patient's mouth or face should be positioned.

The reference or references are preferably "immobile" on the screen, i.e., they do not move on the screen when the acquisition device is moved.

In a preferred embodiment, the reference or references each correspond to an identification mark borne by a related reference frame on the patient, that is to say that the patient did not have before the implementation of the method, preferably borne by a dental retractor. A reference frame may also be a part bitten by the patient.

The identification mark may have an area greater than 0.5 $mm^2$, preferably greater than 1 $mm^2$, preferably greater than 2 $mm^2$, preferably greater than 5 $mm^2$, preferably greater than 10 $mm^2$, even greater than 20 $mm^2$, even greater than 30 $mm^2$, and/or less than 50 $mm^2$.

Large dimensions conferred to an identification mark or an increased number of identification marks advantageously improve the precision of the positioning of the acquisition device.

The identification marks may be identical or different.

The identification marks may, in particular, be different according to their position, for example according to whether they are in the upper or lower part of the reference frame, and in particular of the retractor, or to the right or to the left of the reference frame, and in particular of the retractor.

The identification mark may be identical to or different from the corresponding reference.

It is preferably a geometric shape, for example a point, one or more lines, for example parallel, a star, a circle, an oval, a regular polygon, particularly a square, a rectangle or a diamond.

The identification mark may also be an image, a letter, a number or a sequence of letters and/or numbers.

The identification mark is preferably of a different color from the surface of the retractor that surrounds it, preferably so as to offer a high contrast.

An identification mark may be visible or invisible to the naked eye, as long as it appears on the screen of the acquisition device.

To improve accuracy, the identification marks are preferably spaced apart from each other so that, when they correspond to their respective references on the screen, at least the first and second identification marks are less than 3 cm, preferably less than 2 cm, preferably less than 1 cm, preferably less than 0.5 cm, from the first and second edges, respectively, of the screen. The first and second edges are, preferably, opposite edges of the screen.

The identification mark may have one or more dimensions and/or a shape and/or color identical to or different from the corresponding reference.

"Correspondence" of a reference and an identification mark is a predefined position of one with regard to the other. It indicates a particular positioning of the acquisition device with regard to the identification mark. The correspondence depends on the nature of the reference and the identification mark. The predefined situation, which corresponds to the target acquisition conditions, may notably be a superposition, total or partial, a juxtaposition, or an alignment of the reference and the identification mark.

The exact superposition of the reference and the identification mark not only makes it possible to determine the direction towards which the lens of the acquisition device must point and/or the distance between the acquisition device and the retractor, but also, if the reference and/or the identification mark are asymmetrical, the orientation of the acquisition device around this direction.

The dimensions and/or areas of an identification mark and the corresponding reference and/or the distance between several identification marks and between corresponding references may be used to adjust the distance between the acquisition device and the arches.

The reference may be, for example
- a fixed line, on which the user must, for example, align the identification marks,
- a shape, preferably asymmetrical, corresponding to the shape of an identification mark to superpose, for example, a point that the user must, for example, superpose on the identification mark, or a circle in which the user must for example place the identification mark,
- a colored shape corresponding to the color of an identification mark to superpose,
- a shape complementary to the shape of an identification mark, preferably so that the matching of the identification mark and the reference leads to a shape having a meaning, such as a geometric, shape, a letter or a text, a drawing, or a pattern, for example.

In one preferred embodiment, the references are defined, at least partially, from information provided by the initial reference model. For example, according to the principles of "augmented reality", the reference may be a view of the initial reference model, for example a front view or a right view or a left view of the initial reference model, made visible, transparently, on the screen of the image acquisition device during the acquisition. It is therefore very easy for the patient to approximately superpose such a view with the teeth that they must photograph.

In one preferred embodiment, the acquisition is done by means of an acquisition kit according to the invention including:
- a dental retractor, preferably of a biocompatible material, having an identification mark;
- an image acquisition device, preferably of the type described above, having a display screen for an acquirable image, and a computer program comprising program code instructions for displaying at least one reference on said screen, said reference being preferably immobile on the screen, and arranged in a position called "correspondence position" in which, when the identification mark corresponds to the reference on the screen, the acquirable image represents the retractor in a predetermined angle of view and/or at a predetermined distance.

A kit according to the invention advantageously allows acquisition of images without needing a specialized person, in particular, an orthodontist. Images can be acquired, in particular, by the patient themselves or an associate, with a simple mobile phone, anywhere, and in particular outside a medical, dental or orthodontic office.

Moreover, the image acquisition device does not need to be mechanically stabilized, for example using a tripod or by integration in a device positioned on the ground.

Of course, an acquisition kit does not permit very precise positioning of the acquisition device relative to the teeth.

In particular, the precision of positioning the retractor relative to the teeth is limited. The person who creates the images also positions the image acquisition device in an approximate manner, despite the correspondence of the identification mark with the reference on the screen. As will be seen in more detail in the remaining description, however, the image processing does not require great precision of positioning the acquisition device when acquiring images.

Unlike the prior art, for example described in WO2006/065955, it is not particularly necessary, at the time of acquiring images, to use identification marks whose positioning is perfectly defined with regard to the teeth, in particular because they have been fixed on the teeth themselves or because they result from a local modification, at a specific location, of a tooth, for example by laser. The possibility of acquiring images with a limited precision constitutes a considerable advantage, since it makes this acquisition possible at any place and by any person. The patient no longer needs to go to the orthodontist, in particular.

Preferably, no measurement of the teeth is done to arrange the acquisition device in the correspondence position.

Preferably, no identification mark corresponding to a reference appearing on the screen is directly fixed on the teeth or gums or on a dental arch of the patient.

The acquisition device may, in particular, be a mobile phone and the program may be a specialized app for a mobile phone.

The retractor may have the characteristics of retractors used up to now. It conventionally includes a support provided with a rim extending around an opening and arranged so that the patient's lips may rest therein, leaving the patient's teeth visible through said opening (FIG. 5a and FIG. 5c).

The support, for example of plastic, preferably has an essentially flat shape and a weight of less than 500 g, preferably less than 300 g. The opening is preferably arranged essentially in the center of the support. The opening area is preferably greater than 15 $cm^2$, greater than 30 $cm^2$, greater than 40 $cm^2$, greater than 50 $cm^2$, and/or less than 100 $cm^2$, less than 80 $cm^2$, less than 60 $cm^2$.

Preferably, as shown by FIG. 5a, the retractor has several identification marks, preferably not aligned, preferably coplanar.

Preferably, the retractor has at least three identification marks and the computer program permits displaying one or more corresponding references on the screen of the acquisition device.

In one embodiment, the positioning of the image acquisition device results from the simple matching of references appearing on the screen of said acquisition device with corresponding identification marks, preferably with identification marks of a dental retractor.

In one embodiment, the reference or references that appear on the screen are determined according to the patient and/or the therapeutic treatment. In other words, the computer program is parameterized according to the patient so that the acquired images correspond specifically to the needs of the patient. Advantageously, during image acquisition, the acquisition device is therefore positioned in an essentially optimal position relative to the particular features of the patient and/or the therapeutic treatment applied.

As will be seen in more detail in the following description, the identification marks of the retractor preferably have several functions. First, they permit guiding the positioning of the image acquisition device when acquiring images, using corresponding references appearing on the screen of the acquisition device. They also permit, at step c), cropping the updated images. Finally, the identification marks of the retractor, which appear on the images, permit, at step d), roughly determining virtual acquisition conditions approximating actual acquisition conditions, which accelerates computer processing.

Steps c) and beyond are preferably done either on a personal device of the patient, preferably with the device used at step b), or with an app at a dental healthcare professional, or with a dedicated third-party server.

At step c), each updated image is analyzed so as to create, for each updated image, an updated map relating to at least one discriminant information.

Cropping

The image analysis may include cropping of the updated image to isolate the relevant part, in particular to remove, at least partially, from the updated image the elements that were not the subject of the initial reference model, such as the patient's nose or eyes, or the retractor. This cropping is facilitated by the representation of identification marks on the updated image.

In particular, as shown in FIGS. 5a and 5c, the retractor 10 preferably has at least three nonaligned identification marks 12. If the retractor is in several pieces, for example, conventionally, in two pieces, each piece bears preferably at least three nonaligned identification marks.

The shape of an identification mark, for example an asymmetrical shape, may also be used to identify the position of the retractor in the updated image.

Preferably, the identification marks have shapes and/or colors facilitating their identification in an updated image. For example, they may be black when the rest of the retractor is white.

In one embodiment, the identification marks have shapes and/or colors allowing them to be individually identified. For example, they may each have a different color.

The identification of identification marks in the updated image permits identifying the area of the updated image containing the elements that were the subject of the initial reference model, i.e., the teeth and gums. The updated image may then be cropped accordingly. The comparison of FIGS. 5a and 5b, or 5c and 5d, illustrates the effect of cropping on an updated image.

Updated Map

Figure 6A:
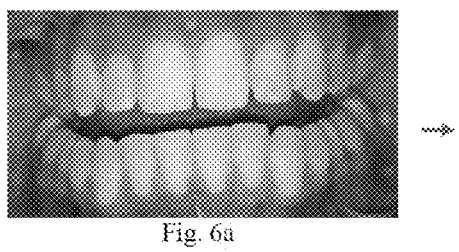
Figure 6B:
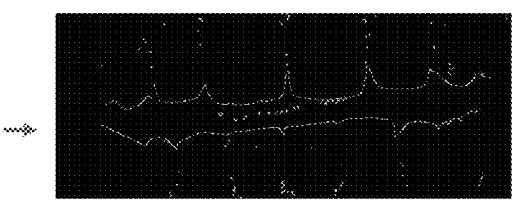

An updated map shows a discriminant information in the reference frame of the updated image. For example, FIG. 6b is an updated map relative to the contour of the teeth obtained from the updated image of FIG. 6a.

The discriminant information is preferably chosen from the group made up of contour information, color information, density information, distance information, brightness information, saturation information, information regarding reflections and combinations of these pieces of information.

The skilled person knows how to process an updated image to show the discriminant information. This processing includes, for example, the application of well-known masks or filters, provided with image processing software. Such processing permits, for example, detecting high contrast regions to determine contours.

This processing notably comprises one or more of the following known and preferred methods, i.e.:
- by applying a Canny filter, in particular to search for contours using the Canny algorithm;
- by applying a Sobel filter, in particular to calculate derivatives using the extended Sobel operator;

by applying a Laplace filter, to calculate the Laplacian of an image;

by blob detection in an image ("Blobdetector");

by applying a threshold to apply a fixed threshold to each element of a vector;

by resizing, by using the relationship between the pixel zones ("Resize(Area)") or bicubic interpolations on the pixel environment;

by image erosion by means of a specific structuring element;

by image dilation by means of a specific structuring element;

by retouching, in particular by using regions in the vicinity of the restored area;

by applying a bilateral filter;

by applying a Gaussian blur;

by applying an Otsu filter, to search for the threshold that minimizes the intraclass variance;

by applying an A* filter, to search for a path between points;

by applying an adaptive threshold to apply an adaptive threshold to a vector;

by applying a histogram equalization filter of a grayscale image in particular;

by blur detection to calculate the entropy of an image by using its Laplacian;

by finding the contours of a binary image;

by flood fill, notably to fill a connected element with a determined color.

The following non-limiting methods, while they are not preferred, may also be implemented:

by applying a mean shift filter, so as to find an object in a projection of the image;

by applying a contrast limited adaptive histogram equalization (CLAHE) filter;

by applying a Kmeans filter to determine the center of clusters and groups of samples around clusters;

by applying a DFT filter so as to do a discrete, direct or inverse Fourier transform of a vector;

by calculating moments;

by applying a Hu moments filter to calculate invariants of Hu invariants;

by calculating the integral of an image;

by applying a Scharr filter, to calculate a derivative of the image by implementing a Scharr operator;

by searching for the convex hull;

by searching for the convexity defects of a contour;

by shape matching ("MatchShapes");

by the point polygon test of a contour; by Harris corner detection;

by searching for minimal eigenvalues of gradient matrices, to detect corners ("CornerMinEigenVal");

by applying a Hough transform to find circles in a grayscale image ("HoughCircles");

By "active contour modeling" (tracing the contour of an object from a potentially "noisy" 2D image;

by calculating a force field, called "gradient vector flow" (GVF), in a part of the image;

by cascade classification;

by deep learning.

Preferably, discriminant information is optimized using an optimization process according to the invention including steps C1 to C3.

At optional step d), the actual acquisition conditions for step b) are roughly determined. In other words, at least the relative position of the image acquisition device at the time the updated image was taken is determined (position of the acquisition device in space and orientation of this device). Step d) advantageously permits limiting the number of tests under virtual acquisition conditions during step e) and therefore permits considerably accelerating step e).

Preferably, one or more heuristic rules are used. For example, preferably, virtual acquisition conditions likely to be tested at step e) are excluded, the conditions that correspond to a position of the image acquisition device behind the teeth or at a distance from the teeth greater than 1 m.

Figure 7:
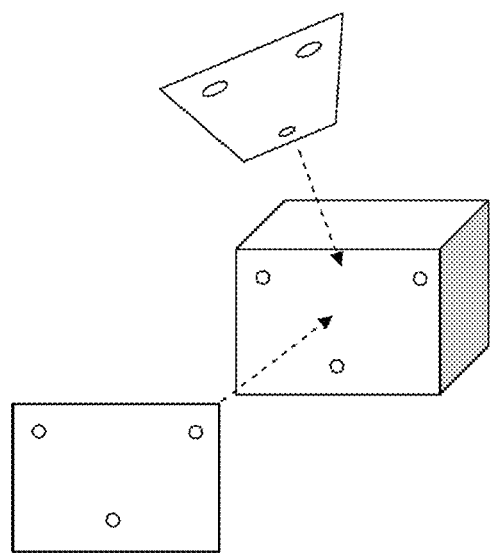

In one preferred embodiment, as illustrated in FIG. 7, the identification marks shown in the updated image are used, and, in particular identification marks 12 of the retractor, to determine an essentially conical region of space defining the virtual acquisition conditions likely to be tested at step e), or "test cone".

Specifically, there are preferably at least three nonaligned identification marks 12 on the retractor 10, for example, and their relative positions on the retractor are precisely measured.

The identification marks are then identified on the updated image, as described previously. Simple trigonometric calculations allow the direction according to which the updated image was taken to be approximately determined. A cone oriented in this direction, whose apex is level with the retractor and whose half-angle at the apex is preferably less than 10°, preferably less than 5°, for example 3° can then be defined as "test cone". The half-angle at the apex corresponds to a degree of uncertainty. The smaller the half-angle at the apex, the greater the probability that the virtual acquisition conditions corresponding to the actual acquisition conditions are outside the test cone.

For example, when the updated image is taken perpendicular to the plane of the three identification marks on the retractor, it can be deduced therefrom that the acquisition device was essentially within a test cone whose axis is essentially perpendicular to this plane when taking the updated image. If the relative positions of the three identification marks in the updated image are different from those which the identification marks occupy on the retractor, the axis of the test cone in which the search for the positioning of the acquisition device is limited during the acquisition of the updated image is inclined relative to the plane of the identification marks, as shown in FIG. 7.

In one particular embodiment as illustrated in FIGS. 5a and 5c, the retractor has independent left and right parts, which each include at least three identification marks, preferably at least four identification marks. A left test cone may then be determined using the identification marks of the left part and a right test cone may be determined by using the identification marks of the right part of the retractor. The virtual acquisition conditions that can be tested can then be limited to positions of the acquisition device in the space belonging to both of these test cones. It may also be considered that the best evaluation of the position of the acquisition device corresponds to the mean position between the best position in the left test cone and the best position in the right search cone.

The position of the identification marks in the updated image also allows the attitude of the acquisition device when capturing the updated image to be evaluated. For example, if it is known that two identification marks are essentially aligned in a horizontal direction when acquiring the updated image, the direction of the straight line containing these two points in the updated image provides an indication of the orientation of the acquisition device under the actual acquisition conditions.

Finally, the size and area of the identification marks on the updated image or their spacing also allow the distance between the image acquisition device and the teeth during acquisition of the updated image to be evaluated, and therefore the test cone to be reduced to a truncated cone.

At optional step d), data provided by the acquisition device concerning its orientation can also be used, for example, gyroscopic data.

Preferably, at step d), the actual calibration of the acquisition device during step b) is roughly determined.

The way each calibration parameter acts on the acquired image is well known. In particular, the functioning of an acquisition device may conventionally be modeled so as to be able to test a particular calibration on the image acquired. The inventors have reversed such a model with no particular technical difficulty, so that, by analysis of the representation of the retractor, it is possible to roughly evaluate the calibration of the acquisition device during step b).

For example, the ratio between the area of the identification marks in the updated image and the area of the updated image allows the focal length of the acquisition device during step b) to be evaluated. The representation of an identification mark whose optical characteristics are known allows the exposure time and sensitivity to be evaluated.

In one preferred embodiment, an identification mark is a relief that does not extend exclusively in the general plane of the retractor, corresponding to a plane parallel to the frontal (or coronal). Preferably, an identification mark is a relief that extends into a plane essentially perpendicular to the general plane of the retractor. The relief may, in particular, have the form of a tab that, when the retractor is in its service position, extends toward the bottom of the mouth.

Analysis of the representation of this relief advantageously permits evaluating the depth of field. Alternatively, two identification marks that are not in the same frontal plane may be used for this purpose.

Step d) only allows a rough assessment of the actual acquisition conditions. Step d) nevertheless allows a restricted set of virtual acquisition conditions likely to correspond to the actual acquisition conditions to be determined, and, in this set, virtual acquisition conditions constituting the best starting point for step e1) described below.

Step d) also allows updated images unsuited for continuing the method to be detected, for example an updated image that does not show the identification marks. Preferably, the method is then resumed at step c) with a new updated image.

Of course, the different methods that may be implemented at step d) may be combined.

The objective of step e) is to modify the initial reference model in order to obtain an updated reference model that corresponds to the updated image. Ideally, the updated reference model is therefore a three-dimensional numerical model from which the updated image could have been taken if this model were real.

Therefore, a succession of reference models "to test" are tested, the choice of a reference model to test being preferably dependent on the degree of correspondence of the reference models "to test" previously tested with the updated image. This choice is preferably made by following a known optimization process, in particular chosen from among metaheuristic optimization processes, preferably evolutionary, and in particular in the processes of simulated annealing.

At step e1), it is determined that the reference model to test is the initial reference model during the first execution of step e2).

At step e2), virtual acquisition conditions to test are initially determined, i.e., a virtual position and orientation likely to correspond to the actual position and orientation of the acquisition device when capturing the updated image, as well as, preferably, a virtual calibration likely to correspond to the actual calibration of the acquisition device when capturing the updated image.

The first virtual acquisition conditions to test may be random. Preferably, they are chosen from the limited set determined at step d), and more preferably correspond to virtual acquisition conditions corresponding, according to step d), to the most promising virtual acquisition conditions, that is to say constituting the best springboard to approach, as quickly as possible, the actual acquisition conditions (step e21)).

The image acquisition device is then virtually configured under the virtual acquisition conditions to test so as to acquire a reference image of the reference model to test under these virtual acquisition conditions to test. The reference image therefore corresponds to the image that the image acquisition device would have taken if it had been positioned, relative to the reference model to test, and optionally calibrated, under the virtual acquisition conditions to test (step e22)).

If the updated image was taken while the tooth position was exactly the one in the reference model to test, and if the virtual acquisition conditions are exactly the actual acquisition conditions, the reference image may therefore be exactly superposed on the updated image. The differences between the updated image and the reference image result from errors in the evaluation of virtual acquisition conditions (if they do not exactly correspond to the actual acquisition conditions) and movements of the teeth between step b) and the reference model to test.

To compare the updated and reference images, the discriminant information in these two images is compared. More precisely, a reference map is created from the reference image representing the discriminant information (step e23)).

The updated and reference maps, both relating to the same discriminant information, are then compared and the difference between these two maps is evaluated with a score. For example, if the discriminant information is the tooth contour, the mean distance between the points of the tooth contour that appears on the reference image may be compared with the points of the corresponding contour that appears on the updated image, the score being higher the shorter this distance.

Preferably, the virtual acquisition conditions include the calibration parameters of the acquisition device. The score is higher the closer the calibration parameter values tested are to the calibration parameter values of the acquisition device used at step b). For example, if the aperture tested is far from the one of the acquisition device used at step b), the reference image has blurry regions and sharp regions that do not correspond to the blurry regions and sharp regions of the updated image. If the discriminant information is the tooth contour, the updated and reference maps will therefore not show the same contours and the score will be low.

The score may, for example, be a correlation coefficient.

The score is then evaluated by means of a first evaluation function. The first evaluation function allows it to be decided whether the cycling in step e2) should be continued or stopped. The first evaluation function may be, for example, equal to 0 if the cycling should be stopped or equal to 1 if the cycling should be continued.

The value of the first evaluation function may depend on the score attained. For example, it may be decided to continue the cycling in step e2) if the score does not exceed a first limit. For example, if an exact correspondence between the updated and reference images leads to a score of 100%, the first limit may be, for example, 95%. Of course, the higher the first limit, the better the precision of the evaluation of the virtual acquisition conditions if the score exceeds this first limit.

The value of the first evaluation function may also depend on the scores obtained with the virtual acquisition conditions tested previously.

The value of the first evaluation function may also depend on random parameters and/or the number of cycles of step e2) already conducted.

In particular, it is possible that despite the repetition of cycles, it is not possible to find virtual acquisition conditions that are sufficiently close to the actual acquisition conditions for the score to reach said first limit. The first evaluation function may therefore lead to the decision to stop the cycling even though the best score obtained did not reach said first limit. This decision may result, for example, from a number of cycles greater than a predetermined maximum number.

A random parameter in the first evaluation function may also allow continuing tests of new virtual acquisition conditions, even though the score appears satisfactory.

The evaluation functions conventionally used in metaheuristic optimization processes, preferably evolutionary, in particular in simulated annealing processes, may be used for the second evaluation function.

If the value of the first evaluation function indicates that it is decided to continue cycling in step e2), the virtual acquisition conditions tested (step e25)) are modified and a cycle is started again (step e2)) consisting of making a reference image and a reference map, and then comparing this reference map with the updated map to determine a score.

The modification of the virtual acquisition conditions corresponds to a virtual movement in space and/or a change in the orientation and/or, preferably, a change in the calibration of the acquisition device. This change may be random, as long as the new virtual acquisition conditions to test still belong to the set determined at step d). The change is preferably guided by heuristic rules, for example by favoring changes that, according to an analysis of the previous scores obtained, appear the most favorable for increasing the score.

Figure 12A:
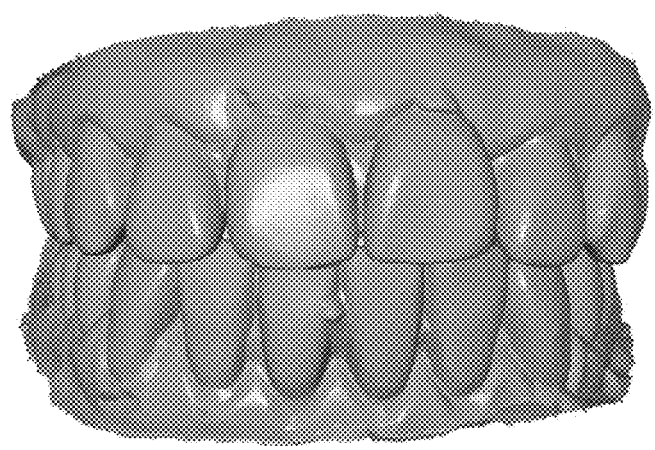
FIGS. 12a and 12b illustrate two views of a three-dimensional model with two different focal lengths.
Figure 12B:
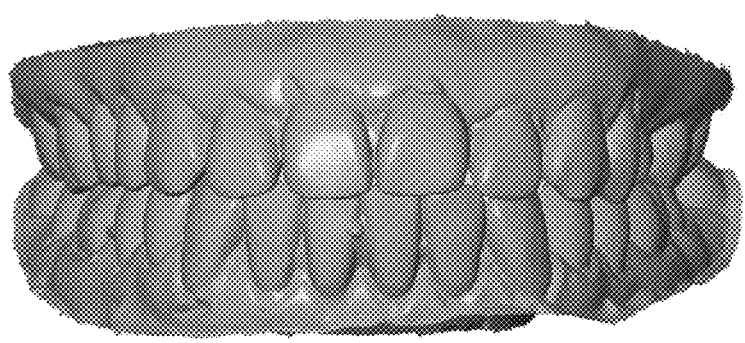

For example, FIGS. 12a and 12b illustrate the effect of a modification of the virtual acquisition conditions, in this case, a modification of the focal length, on the reference image.

The cycling in e2) is continued until this value of the first evaluation function indicates that it is decided to leave this cycling and continue to step e3), for example if the score reaches or exceeds said first limit.

The virtual acquisition conditions at step e2) are preferably optimized by using a metaheuristic method, preferably evolutionary, preferably a simulated annealing algorithm. Such an algorithm is well known for nonlinear optimization.

If the cycling is left in step e2), without being able to obtain a satisfactory score, for example without the score being able to reach said first limit, the process may be stopped (failure situation) or resumed at step c) with a new discriminant information and/or with a new updated image. The process may also be continued with virtual acquisition conditions corresponding to the best score attained. A warning may be emitted in order to inform the user of the error in the result.

If the cycling is left in step e2) with a satisfactory score being able to be obtained, for example because the score reached or even exceeded said first limit, the virtual acquisition conditions essentially correspond to the actual acquisition conditions.

Preferably, the virtual acquisition conditions include the calibration parameters of the acquisition device. The process conducted therefore allows the values of these parameters to be evaluated without needing to know the nature or settings of the acquisition device. Step b) may therefore be conducted with no special precautions, for example by the patient themselves using their mobile phone.

Moreover, the actual calibration is sought by comparing an updated image with views of an initial reference model under virtual acquisition conditions that are tested. Advantageously, it does not require the updated image to show a calibration gauge, that is to say a gauge whose characteristics are precisely known, to determine the calibration of the acquisition device.

WO2006/065955 incorporated for reference, describes the use of images to create three-dimensional models in the field of orthodontic treatments. However, this document does not describe a method for using simple photographs, conventionally presenting partial images of the teeth, portions of blurred images and variable reflections, taken generally in a non-simultaneous manner, without the need to select noteworthy points in the images, and with an acquisition device whose calibration is not known.

In a method for checking the position of teeth according to the invention, the updated images are not used to create a totally new updated three-dimensional model, but rather only to modify the initial, very precise, reference model. A totally new updated three-dimensional model created from simple photographs taken with no special precautions would be, in particular, too imprecise for a comparison with the initial reference model to be able to lead to conclusions on tooth movement.

Differences may exist between the determined virtual acquisition conditions and the actual acquisition conditions, in particular if teeth move between steps a) and b). The correlation between the updated and reference images may then still be improved by resuming step e2), the reference model to test being then modified by moving one or more tooth models (step e3)).

The search for the reference model best approximating the positioning of the teeth during the acquisition of the updated image may be performed like the search for the virtual acquisition conditions best approximating the actual acquisition conditions (step e2)).

In particular, the score is evaluated by means of a second evaluation function. The second evaluation function allows it to be decided whether the cycling in steps e2) and e3) should be continued or stopped. The second evaluation function may be, for example, equal to 0 if the cycling should be stopped or equal to 1 if the cycling should be continued.

The value of the second evaluation function preferably depends on the best score obtained with the reference model to test, that is to say the differences between the updated and reference maps, under the virtual acquisition conditions best approximating said actual acquisition conditions.

The value of the second evaluation function may also depend on the best score obtained with one or more reference models tested previously.

For example, it may be decided to continue the cycling if the score does not exceed a second minimum limit. The value of the second evaluation function may also depend on random parameters and/or the number of cycles of steps e2) and e3) already conducted.

The evaluation functions conventionally used in metaheuristic optimization processes, preferably evolutionary, in particular in simulated annealing processes, may be used for the second evaluation function.

If the value of the second evaluation function indicates that it is decided to continue the cycling in steps e2) and e3), the reference model to test is modified and a cycle is started again (steps e2) and e3)) with the new reference model to test.

The change in the reference model to test corresponds to a movement of one or more tooth models. This change may be random. The change is preferably guided by heuristic rules, for example by favoring changes that, according to an analysis of the previous scores obtained, appear the most favorable for increasing the score.

Preferably, the movement of a tooth model is sought that has the greatest impact on the score, the reference model to test is modified by moving this tooth model, then the cycling in steps e2) and e3) is continued so as to optimize the score. Then the tooth model with the greatest impact on improving the score may be sought among the other tooth models, and the optimal movement of this other tooth model on the score may be sought. This may be continued for each tooth model.

Next, it is possible to resume a cycle on all the tooth models and continue thus until a higher score than the second limit is obtained. Of course, other strategies may be used to move one or more tooth models in the reference model to test and search for the maximum score.

Cycling in steps e2) and e3) is continued until the value of the second evaluation function indicates that it is decided to leave this cycling and continue to step f), for example if the score reaches or exceeds said second limit.

The reference model with cycling in steps e2) and e3) to search for the tooth model positions that optimize the score is preferably sought by using a metaheuristic method, preferably evolutionary, preferably a simulated annealing algorithm. Such an algorithm is well known for nonlinear optimization.

If the cycling is left in steps e2) and e3), without being able to obtain a satisfactory score, for example without the score being able to reach said second limit, the process may be stopped (failure situation) or resumed in step c) with a new discriminant information and/or with a new updated image.

If it is decided to restart the process at step c) from another discriminant information and/or another updated image because the first limit or the second limit has not been reached, the choice of the new discriminant information and/or the new updated image may depend on the scores obtained previously, in order to favor the discriminant information and/or the updated image which, in view of these scores, appear the most promising.

A new discriminant information, obtained, for example, by combination of other discriminant information already tested, may be used. If applicable, it may also be necessary to acquire one or more new updated images. Preferably, indications are provided to guide the positioning of the acquisition device for the capture of this new updated image. For example, the patient may be told that they should take a photo of the right part of their lower arch.

If the cycling is left in steps e2) and e3) without being able to obtain a satisfactory score, the process may also be continued with the reference model and under the virtual acquisition conditions corresponding to the best score attained. A warning may be emitted in order to inform the user of the error in the result.

If the cycling is left in steps e2) and e3) with a satisfactory score being able to be obtained, for example because the score has reached or even exceeded said second limit, the virtual acquisition conditions essentially correspond to the actual acquisition conditions and the tooth models in the reference model obtained (called "updated reference model") are essentially in the position of the patient's teeth at the time of step b).

The cycling in steps e2) and e3) advantageously permits improving the evaluation of the acquisition device calibration parameters at step b).

At step f), the updated reference model resulting from optimization by movement of the tooth models is compared with the initial reference model. The updated reference model essentially corresponds to the updated image. The comparison of step f) therefore allows the differences between the positioning of the teeth at step a) (initial reference model) and during the acquisition of the updated image (step b)) to be observed. The process thus permits precisely determining, for each of the teeth, the movements between these two steps.

By repeating steps b) and beyond, it is also possible to evaluate the speed of evolution of the tooth position, and thus to measure, for example, the efficacy of an orthodontic treatment. A method for checking the positioning of teeth according to the invention may, for example, be used to remotely monitor the evolution of an orthodontic treatment and thus to optimize patient appointments with their orthodontist.

In a preferred embodiment, the checking method according to the invention is implemented several times for the same patient, preferably successively with several discriminant information, preferably more than 2, more than 3, more than 5 discriminant information for each updated image and/or with several updated images, preferably more than 2, more than 3, more than 5 updated images. The evaluation of the movement of a tooth may thus be refined by considering the different scores obtained. The comparison of these scores also permits, if applicable, discarding unsatisfactory discriminant information and/or updated images.

Depending on the movement measured, practical information may be generated. If the movement is small, this practical information may be that no action is to be undertaken. In contrast, if one or more teeth have perceptibly moved, the information may be to schedule a visit with the dentist or orthodontist. Preferably, the practical information depends on the extent of movement of the teeth. In one embodiment, an appointment may automatically be made with the dentist or orthodontist, depending on the amplitude and/or nature of the movements detected.

In one embodiment, the practical information is used to modify the time interval after which the patient should be alerted that a new updated image should be created.

In one embodiment, the individual device permits displaying images, or even a sequence of images showing the positioning of the teeth on different dates. These images may be presented in the form of an animation, for example, in the form of a slide show or a movie.

Preferably, the image acquisition device is a telephone that allows sending the results obtained by the implementation of the method, preferably in a secure manner.

The communication may for example be carried out, at least in part, over the airwaves, preferably according to at least one protocol chosen from edge, 3G, 4G, udmsa, hpdmsa, Bluetooth, and Wi-Fi protocols, or by any other protocol, suitable for mobile or nomadic devices, by wired synchronization with the personal computer, or by optical transmission.

As can clearly be seen in this document, a method for checking the positioning of teeth according to the invention permits a precise and effective monitoring of the position of the patient's teeth, essentially without imposing on the patient. In particular, simple photographs taken with no special precautions, for example with a mobile phone, are sufficient. The patient may therefore easily implement this process.

Detailed Description of a Method for Adjusting a Worn Orthodontic Appliance

The orthodontic appliance worn by the patient may be the first orthodontic appliance initially provided to them for their orthodontic treatment or a replacement appliance made available to them later.

The first orthodontic appliance may be created according to a conventional method.

In particular, for a treatment by means of aligners, the orthodontist can, at the beginning of the treatment, determine a first series of aligners suited for the teeth to reach a position corresponding to an objective reference model, preferably representing a final set-up, created according to step b'), as described below. This determination may be done conventionally.

Preferably, only the first aligner of this first series is created and provided to the patient.

The possibility of evaluating the positioning of the teeth from simple photographs, taken with no particular precautions, in particular with a mobile phone, permits increasing the number of checkups during an orthodontic treatment. The treatment can therefore be adjusted very regularly, in particular by adjusting or switching out the orthodontic appliance.

Generically, a "replacement orthodontic appliance" is an appliance resulting from this treatment adjustment. The replacement orthodontic appliance may therefore be the orthodontic appliance that was worn to that point, designated by "worn orthodontic appliance" and adjusted, for example by switching out the orthodontic archwire attached to the teeth or modifying its tension. The replacement orthodontic appliance may also be a new orthodontic appliance, especially when active aligners are used for the treatment.

Figure 14:
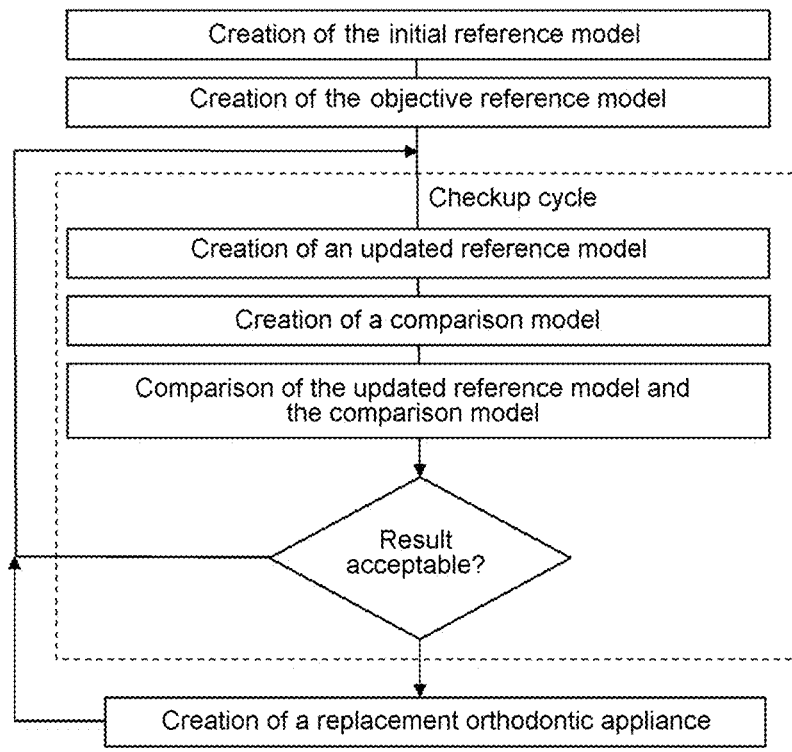
FIG. 14 is a flowchart illustrating the implementation of an adjustment method for an orthodontic appliance according to the invention.

A method for adjusting an orthodontic appliance according to the invention includes steps a') to f') described above, and illustrated in FIG. 14.

Step a') is identical to step a) and may include one or more of the optional characteristics of step a) described in this description. It leads to an initial reference model that numerically represents, in three dimensions, at the least the part of the arches that includes the teeth of the patient to treat. The initial reference model may be created by all known conventional methods.

Step a') is preferably the first step. In particular, the objective reference model s conventionally determined from the initial reference model.

Step b') consists of creating an objective reference model that numerically represents, in three dimensions, the teeth to treat in a position to be achieved at a treatment time point, in particular at the end of the treatment ("final setup") or at a predetermined intermediate treatment step ("intermediate setup"), for example at a planned time point to switch out the aligner or modify the tension of the orthodontic archwire.

All the "intermediate setups" may be created at the beginning of treatment. The number of intermediate setups may be greater than 1, than 2, than 10, than 20, than 30, than 40, than 50 or than 60. The duration between two successive intermediate setups may be, in particular, less than 10 weeks, than 8 weeks, than 6 weeks, than 4 weeks, than 2 weeks or than one week.

The objective reference model may be created by all known conventional methods.

Preferably, the objective reference model results from a deformation of the initial reference model. In particular, preferably, the tooth models that correspond to the teeth to treat are conventionally moved virtually until they reach their desired position.

Alternatively, a physical model, for example of plaster, representing the teeth in their desired position may also be created, then scanned in three dimensions.

Step b') is preferably conducted essentially at the same time as step a'). However, it may be conducted at any time until the first use of the objective reference model.

Step c') of creating an updated reference model is identical to steps b) to e) and may include one or more of the optional characteristics of these steps described in this description.

It is preferably executed at the time when the orthodontist decides that the patient should have a checkup of the efficacy of their treatment, for example more than 1 week or more than 2 weeks after step a') of creating the initial reference model. It may also be decided by the patient or scheduled.

The updated initial reference model is obtained by deformation of the initial reference model, preferably by movement of the tooth models, by using information resulting from the updated images. More precisely the deformation is optimized, preferably by an evolutionary method, preferably by simulated annealing, for the updated images best fitting the views of the deformed initial reference model, then called "updated reference model". In other words, these views are essentially identical to the updated images.

Preferably, the updated reference model is made accessible to the orthodontist in real time. In particular, if it is determined with a patient's device, for example their phone, it may be sent to the orthodontist. Advantageously, the orthodontist is then alerted and may intervene accordingly.

The use of only updated images without the initial reference model does not permit a precise three-dimensional model to be constructed. It is the use of these images to modify the initial reference model (which is of high precision, notably when it is obtained by a scan) which leads to a precise updated reference model, even though the updated images were taken with no special precautions.

The updated reference model therefore provides the positioning parameters at the time when the updated images are acquired for the points of the teeth.

Preferably, the value of a positioning parameter for a point of a tooth, for example the centroid of the tooth, is shown on a graph.

Preferably, the graph shows, for each checkup cycle, the value of this positioning parameter, for this point of the tooth. Preferably, a curve connects these points. More preferably, the time scale, preferably on the x-axis, is linear. The treatment dynamics regarding this parameter are advantageously immediately perceptible. The orthodontist and/or the patient may therefore immediately perceive a loss of efficacy of the orthodontic appliance and act accordingly.

Step d') of determining a comparison model may be executed at any time before step e').

Preferably, the comparison model provides theoretical positions of the teeth, or points of the teeth, at intermediate time points between the start and the end of treatment. Preferably, the comparison model is a numerical three-dimensional model. It advantageously permits a visual comparison with the updated reference model. Preferably, the theoretical position of a tooth or a point of a tooth results from a processing of the initial reference model and the objective reference model, in particular, an interpolation, preferably nonlinear, between the positions of this tooth or this point between these two models.

For example, the position (x,y,z) of a point M of a tooth can be defined in a three-dimensional coordinate system, for example orthonormal. The position of this point in the initial reference model, at time point to, and in the objective reference model, at time point $t_G$, may be denoted $(x_0,y_0,z_0)$ and $(x_G,y_G,z_G)$, respectively. If it is considered that the movement is rectilinear and evolves linearly with time, the theoretical intermediate position of this point at intermediate time point $t_i$ in the middle of treatment will be $(x_i,y_i,z_i)$, with $x_i=(x_0+x_G)/2$, $y_i=(y_0+y_G)/2$ and $z_i=(z_0+z_G)/2$.

More preferably, the comparison model depends on one or more previous updated reference models and/or several previous comparison models (established during the previous checkup cycles, i.e., in particular, previous steps c')). The precision is considerably improved.

Preferably, the determination of the comparison model depends on the evolutions between several updated reference models, preferably successive. For example, updated reference models may have been created three months, two months and one month prior, at $t_{-3}$, $t_{-2}$ and $t_{-1}$, respectively. The movement of the centroid of a tooth along the Ox) axis between $t_{-3}$ and $t_{-2}$ may be, for example, 100 µm and the movement between $t_{-2}$ and $t_{-1}$ may be 80 µm. By simple linear extrapolation, it may be considered that the movement along the Ox) axis, between and the present $(t_0)$, will be 60 µm, which permits creating a comparison model at $t_0$ with high precision.

All the conventional prediction methods may be used, a prediction method being a method to establish, from a predictive model, a prediction according to known data.

A predictive model is therefore a model to simulate the future movement of the teeth from past data, and notably past movements of said teeth and/or the past or calculated behavior of the orthodontic appliance.

Preferably, the predictive model considers the action of the orthodontic appliance on the teeth. Thus, in the example above, if it is known that the action of the orthodontic appliance on the movement of the centroid of a tooth along the Ox) axis decreases with time, the movement along the Ox) axis between $t_{-1}$ and the present $(t_0)$ may be estimated at 50 µm and not at 60 µm.

Tools to simulate tooth movements between two extreme positions by considering interactions between the teeth, such as Align Technology's Clincheck, Orametrix's Suresmile®, Harmony's Virtual Setup or Ormco's Insignia, are well known. Preferably, a model of the orthodontic appliance is also used permitting simulating its action, over time, on the teeth, according to their positions, and especially their position in the initial reference model and/or their position in the updated reference model. As can be seen in more detail in the following description, an evaluation method of the behavior of an orthodontic appliance according to the invention allows designing and/or refining such predictive models.

Preferably, a dynamic model is constructed, capable of providing the theoretical position of the teeth or a set of points of the teeth, preferably for each tooth model, at any time point between the start and end of the treatment or, more generally, between the time points corresponding to the initial and objective reference models. Software can be used for this purpose.

Step d') may be done immediately after steps a') and b') have been done, for example less than 3 months, less than one month, or less than one week after steps a') and b') have been done.

Preferably, the comparison model is determined to correspond to a simulation of the position of the teeth treated at a time point $t_c$ as close as possible to the time point of executing step c'), and in particular the time point $t_a$ at which the updated images were acquired. Preferably, these two time points are separated by less than 1 month, less than two weeks, preferably less than one week, preferably less than one day.

Figure 13:
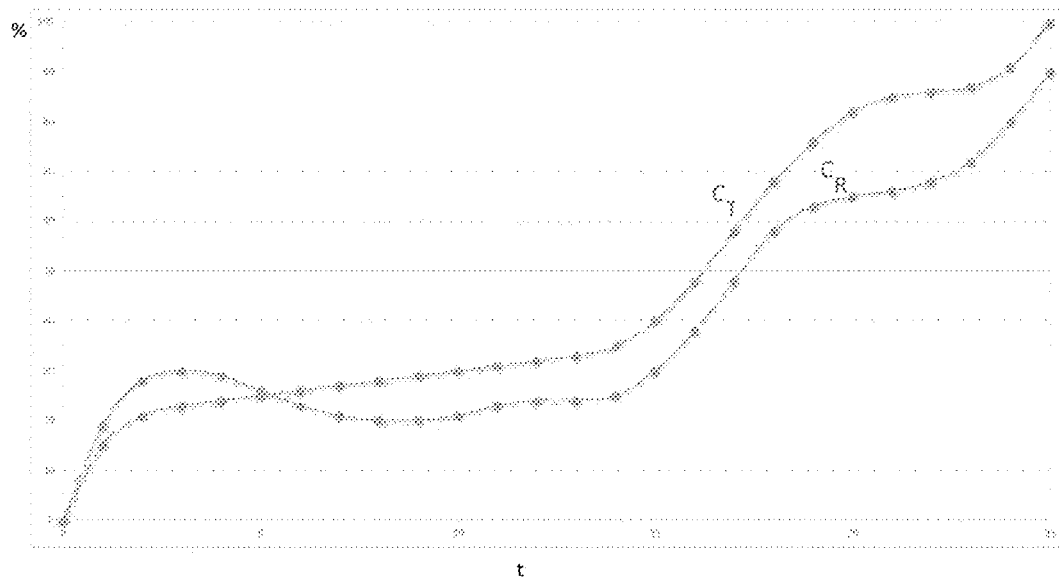
FIG. 13 is an example of the actual and theoretical evolution of the value of a movement quantity parameter, as a function of time. The x-axis provides the time in weeks. The y-axis provides the value of the parameter, in percentage relative to the value desired at the end of treatment.

In FIG. 13, the two time points $t_c$ and $t_a$ are merged, which is especially possible when a dynamic three-dimensional model is available, capable of providing the theoretical position of the teeth at any time point between the start and the end of treatment. If time point $t_a$ is known, it is sufficient to choose the dynamic model at time point $t_a$ as the comparison model.

In one embodiment, the comparison model is always the objective reference model. The precision of adaptation of the orthodontic appliance is not optimal, however.

At step e'), the updated reference model, which corresponds to the situation observed at the time of the checkup, is compared with the theoretical comparison model.

The comparison may be done by the patient and/or the orthodontist.

The comparison preferably includes a determination, for each point of a set of points of the teeth of the updated reference model, preferably for at least three non-coplanar points of each tooth of the updated reference model, of the movement (vector) between the representations of this point on the comparison and updated models. This movement is preferably quantified using the distances and/or angles in a three-dimensional Oxyz coordinate system, for example in an orthonormal coordinate system. The movement may be, for example, determined in Cartesian or cylindrical coordinates.

The analysis of the movement of several points of teeth may be difficult to present or analyze. The points of the same tooth are considered as rigidly linked to one another. Preferably, the analysis of the movement of the points of the same tooth is generalized to evaluate the movement of all the points of this tooth, i.e., the movement of the corresponding tooth model.

In particular, knowledge of the movement of three non-coplanar points of a tooth makes it possible to evaluate the movement of this tooth between its representation (that is, the corresponding tooth model) in the updated reference model and its representation in the comparison model, or "amount of motion". The amount of motion can be expressed by differences in the values of a set of positioning parameters for fixing the position and orientation of an object in space, for example the Cartesian coordinates of a point of the tooth, for example its centroid, and values of angles around a fixed reference, for example orthonormal (differences between the values in the updated reference model and in the comparison model).

Preferably, for each of the positioning parameters, the path to be traveled from the updated reference model is determined in order to attain the comparison model, for example the distance to be traveled by the centroid of the tooth along each of the axes of a fixed orthonormal marker and the rotation to be made around each of these axes.

Preferably, at step e'), the movement speed of the points considered is evaluated, preferably using the initial reference model, and preferably one or more updated reference models determined previously, in particular during previous checkup cycles. The movement speed of a point of a tooth, in one direction, between two successive updated reference models, can be simply evaluated by dividing the distance between the representations of this point on these two models, along this direction, by the time passed between the creation of these two models.

More preferably still, the slowing or acceleration of the movement of the points of the teeth is evaluated by comparison of the speeds of the two successive periods.

If the objective reference model is a final or intermediate setup, the comparison allows evaluation of the movement quantities still necessary to complete the treatment or in order to finish the intermediate step of the treatment, respectively. The comparison also allows evaluation of the movement speed of the teeth up to the end of the intermediate step or the end of the treatment, respectively.

However, this comparison does not allow precise estimation of whether the treatment is proceeding as planned if it is not done at a time point close to the end of the intermediate step or the end of treatment. The detection of an abnormal situation, or more generally a situation requiring an adjustment of the orthodontic appliance, therefore requires substantial analysis capacities.

This is why, preferably, as indicated above, the comparison model is a model that corresponds to an estimation of the expected tooth position essentially at time point $t_a$ of step c'), for example determined at the start of treatment or following the immediately preceding checkup cycle.

The comparison between the actual situation, evaluated with the updated reference model determined at step c'), and the expected situation, evaluated with the comparison model, allows it to be determined whether the orthodontic appliance is correctly fulfilling its function.

If applicable, it also allows it to be determined what the problem is, for example, too much force on a tooth along a direction.

The result of the comparison is considered unsatisfactory if a deviation between the updated reference model and the comparison model exceeds a threshold value. For example, if the comparison model corresponds to a positioning of the teeth envisaged for the time point of the creation of the updated reference model, a deviation of more than 50 μm of the position of the centroid along the axis Ox) can be considered as unsatisfactory. If the comparison model is the objective reference model, the threshold value to exceed for a deviation to produce an unsatisfactory result naturally depends on the remaining time planned to attain the positioning corresponding to the objective reference model.

The comparison preferably leads to a quantification of the deviations, preferably done and presented by a computer. The computer preferably presents the results of the comparison highlighting the most significant deviations.

The comparison may also be visual. Preferably, an orthodontist views and compares the updated reference model and the comparison model. Preferably, a computer screen shows an image highlighting the deviations.

The decision that a deviation is unsatisfactory or not may depend on the orthodontist's decision and/or the result of a computer calculation.

Preferably, the comparison done at step e') leads to recommendations that are presented to the orthodontist. In particular, the method allows the behavior of the orthodontic appliance to be finely determined, and therefore determination of the factor or factors that should be modified to optimize its efficacy.

In one embodiment, step e') leads to generating a report specifying how to modify the tension of the orthodontic appliance archwire in place or how to create a new aligner.

In one embodiment, step e') leads to generating an "updated" score that may be compared to a reference score for equivalent treatments. Preferably, these scores are presented to the patient. Advantageously, the success of the treatment is presented as a fun objective, the scores motivating the patient, and especially children, to comply with the treatment as closely as possible in order to increase their updated score.

Preferably, step e') leads to generating information showing the patient the situation and the different options that are presented. In the event of an unsatisfactory deviation, the patient may, for example, decide to prolong their treatment or choose a new objective reference model.

Preferably, the results of the comparison are sent, preferably in real time, to the patient, preferably on their mobile phone. Advantageously, the patient may thus become aware of the consequences of poor treatment compliance.

At step f'), if the result is unsatisfactory, a replacement orthodontic appliance is created, by modifying the currently worn orthodontic appliance or by creating a new orthodontic appliance.

Step f') is a step conventionally executed during an orthodontist checkup.

According to the invention, a replacement orthodontic appliance is only created, however, if the checkup, preferably performed remotely, indicates that it is necessary.

In one embodiment, the replacement appliance is created remotely, so that, when the patient comes to the orthodontist, the replacement orthodontic appliance may be immediately positioned. In particular, an orthodontic archwire or an aligner may be prepared from the evaluation done at step e'). The orthodontic archwire or the aligner may be created in a laboratory away from the orthodontist's office and then sent by mail to this office.

In one embodiment, the aligner may be directly sent to the patient, with no involvement of the orthodontist.

Preferably, at step f'), the treatment plan is modified according to the modification made to the orthodontic appliance.

In one embodiment, several replacement orthodontic appliances able to immediately replace the worn appliance are determined, preferably according to the treatment speed desired by the patient, an increased speed potentially corresponding to additional pain. Preferably, the choice of the treatment speed is offered to the patient and the replacement orthodontic appliance to be created is determined accordingly.

Of course, at step f'), if the result is unsatisfactory, a series of replacement orthodontic appliances can be created and, preferably, sent to the orthodontist or the patient.

In particular, like at the beginning of the treatment with aligners, a new series of aligners can be determined that is suitable for attaining a tooth position corresponding to the objective reference model. This determination may be done conventionally. Preferably, however, a single aligner is manufactured, and preferably sent to the patient.

Checkup Cycles

Preferably, the method includes several checkup cycles including steps c'), d), e') and f'), preferably each carried out at a time point, for example, determined at the beginning of treatment and/or at the orthodontist's request and/or at the patients initiative.

Two consecutive checkup cycles are preferably separated by a duration of less than 10 weeks, preferably less than 8 weeks, preferably less than 6 weeks, preferably less than 4 weeks, preferably less than 3 weeks, preferably less than 2 weeks.

Preferably, the number of checkup cycles during the treatment is greater than 1, greater than 3, greater than 5, greater than 10, greater than 15, or even greater than 20.

Preferably, a reminder is sent to the patient, for example by SMS, so that they can do a checkup cycle.

In one preferred embodiment, the comparison model of a step d') of a checkup cycle is determined from the updated reference model produced in step c') of a previous checkup cycle, in particular the immediately preceding checkup cycle, or from several updated reference models made during steps c') of previous checkup cycles, for example by extrapolation.

FIG. 13 illustrates a method that has several checkup cycles. It represents the curves of the theoretical ($C_T$) and actual ($C_R$) evolutions over time of an amount of motion parameter of a tooth, and more precisely, the evolution over time of the position of a point M of a tooth, for example, the centroid of this tooth, along the Ox axis, as a percentage of the desired value at the end of treatment.

A checkup cycle is done every week.

Each week, one point of each curve was thus determined, using a comparison model based on a dynamic model simulating an anticipated evolution of the teeth of the initial reference model (point of the curve $C_T$), and an updated reference model based on photographs taken by the patient that week (point of the curve $C_R$).

The first checkup cycles allowed a drift to be observed very quickly. The orthodontic appliance tended to move point M too quickly. This information was presented to the orthodontist, with recommendations on how to modify the orthodontic appliance, for example to specify that the tension exerted by the orthodontic archwire between two given teeth should be reduced.

An appointment between the patient and the orthodontist was set up for the third week. The orthodontic appliance was modified during this appointment. This modification led to bringing the two curves closer together in the subsequent weeks.

After five weeks, the two curves crossed. The orthodontic appliance was therefore again modified at week 8. The two curves then slowly moved closer together, until week 18.

They then diverged perceptibly again, which led to again modifying the orthodontic appliance at week 20.

At the end of week 25, the objective was essentially attained, within the timeframe initially planned. The treatment is then completed.

In one embodiment, the patient receives, for example on their phone, information enabling them to compare the updated reference model and the objective reference model, for example graphical representations of these two models. If the objective reference model represents the teeth at the end of treatment ("final setup"), they may therefore decide themselves to end the treatment.

The theoretical evolution over time curve may be determined, in its entirety, from the beginning of the treatment, by considering modifications in the orthodontic appliance planned during the treatment.

This curve may also be recalculated depending on the modifications made to the orthodontic appliance that were not initially planned. For example, if the modification of the orthodontic appliance done in week 3 was not initially planned, the predictive model used to establish the comparison model used after week 3 and therefore the theoretical evolution over time curve, were preferably modified to take this unplanned modification into account. The predictive model has thus advantageously taken into account a much slower evolution of the movement of point NI along axis Ox) than the one that was initially anticipated.

As it is now clear, the adjustment method according to the invention notably allows a diagnosis of the situation, even the creation of a replacement orthodontic appliance, without the patient having to go to an orthodontist.

Detailed Description of a Method for Evaluating the Behavior of an Orthodontic Appliance Increasing the number of checkup cycles will advantageously allow acquisition of a large amount of data to establish correlations between the parameters of the orthodontic appliance, its behavior and the configurations of the teeth.

Preferably, the parameter values of the orthodontic appliance used initially, as well as, at each checkup cycle, the parameters of the replacement orthodontic appliance, are recorded in a computer. The parameters of the orthodontic appliance comprise intrinsic parameters, such as the material or the shape of an aligner, or the material and the diameter of an orthodontic archwire. They also comprise extrinsic parameters, resulting from its use, such as attachment points for the orthodontic archwire on the teeth or the tension of the orthodontic archwire.

This computer also has access to the different three-dimensional models established as part of the treatment.

An analysis module permits comparing all the data collected, according to conventional statistical methods. This results in a better understanding of the behavior of the orthodontic appliance, depending on the values of its parameters and the configurations of the corresponding teeth.

Preferably, the collected data come from several treatments, preferably from more than 10, more than 100, more than 1,000, more than 10,000, more than 100,000 treatments.

The precision of the statistical analysis is improved.

The data thus allow it to be observed that, in similar configurations of teeth, a type of orthodontic appliance or a parameter of an orthodontic appliance is particularly effective to ensure movement in a particular direction.

They therefore permit modeling the behavior of the orthodontic appliance with high precision, and therefore better evaluating, in a particular situation, its future behavior.

In one embodiment, data analysis permits quantifying the difficulty of a treatment, by comparison of this treatment with equivalent treatments. The orthodontist may therefore inform the patient about the chances of success and the nature of the potential difficulties. The orthodontist may also advantageously decide to modify the treatment initially envisaged, notably by modifying the intermediate setups.

The knowledge thus acquired may therefore be used to optimize
  the design of the orthodontic appliances, and/or
  the choice of an orthodontic appliance for a particular treatment and/or
  the establishment of a diagnosis by the orthodontist, and/or the creation of a replacement orthodontic appliance, and/or the determination of a predictive model to create the comparison model.

This optimization may advantageously cause the orthodontist or the orthodontic appliance designer to consider a parameter of the orthodontic appliance that is conventionally considered negligible.

Advantageously, correlations between parameters of the orthodontic appliance and its behavior can be established without it being necessary to theoretically understand this correlation, i.e., to understand how these parameters produce this behavior.

Detailed Description of a Method for Checking Shape the Teeth

The invention also concerns a method for checking the shape of a patient's teeth. At step a), the definition of tooth models, however, is not indispensable for this checkup.

Preferably, at step e), for each updated image, an updated reference model is sought corresponding to shape of the teeth when the updated image is acquired, the search preferably being done by means of a metaheuristic method, preferably evolutionary, preferably by simulated annealing, in particular by means of one of the metaheuristic methods described previously.

Preferably, as described for step e), this search includes two nested optimization loops.

During the first optimization operation, first, in a reference model to test, which is initially the initial reference model, the virtual acquisition conditions that best correspond to the actual acquisition conditions are optimized. In particular, the virtual position of the acquisition device relative to the reference model to test is sought that offers the view of this reference model to test, i.e., the reference image, which is the closest to the updated image.

Preferably, as described previously, a virtual calibration is also sought that is likely to correspond to the actual calibration of the acquisition device when the updated image is captured.

During the second optimization operation, the reference model to test is then modified, the first optimization operation is started again, and then these two operations are repeated until the reference model to test and the virtual position of the acquisition device are found that make it possible to obtain the reference image that is closest to the updated image.

These operations are similar to those described for the method for checking the positioning of the teeth and the optional characteristics of that checkup are optionally applicable.

However, according to the method for checking the positioning of the teeth described previously, modification of the reference model results from the movement of one or more tooth models. No deformation of the tooth models or the initial reference model is necessary.

To check the shape of the teeth, the modification of the reference model results from a modification of the shape of the reference model to test, in particular one or more tooth models. No movement of the tooth models is necessary.

Of course, it is preferable to do both types of modifications of the reference model to test in order to determine an updated reference model that considers both the movement of the teeth and their deformation.

For example, a third optimization operation may be implemented relating to the movement of the teeth and straddling the first two optimization operations, the second optimization relating to the shape of the tooth models or the reference model to test. It is also possible to implement only the first two optimization operations, by modifying, optionally simultaneously, the shape and position of the tooth models during the second optimization operation.

A third optimization operation may also be implemented relating to the shape of the tooth models or the reference model to test and straddling the first two optimization operations, the second optimization operation relating to the movement of the tooth models. For example, first an updated reference model "to test" is sought, taking into account, at best, the movement of the tooth models, the updated reference model to be tested corresponding to the updated reference model of a step e) of a method for checking the positioning of the teeth described above, and then whether a deformation of the updated reference model to test may lead to a better match with the updated image is researched. For this research, the updated reference model to test is deformed, the first two optimization operations are restarted, then, depending on the match obtained, the research is stopped or continued by doing a new deformation of the updated reference model to test and by relaunching an execution of the first two optimization operations.

Preferably, the first optimization operation and/or the second optimization operation and/or the third optimization operation, preferably the first optimization operation and the second optimization operation and the third optimization operation implement a metaheuristic method, preferably evolutionary, preferably simulated annealing, in particular one of the metaheuristic methods mentioned previously.

Preferably, to check the deformation of the teeth, step e) includes a first optimization operation to search for virtual acquisition conditions best corresponding to the actual acquisition conditions in a reference model to test determined from the initial reference model, and a second optimization operation to search, by testing a plurality of said reference models to test, for the reference model best corresponding to the shape of the patient's teeth when the updated image is acquired at step b), preferably best corresponding to the shape and positioning of the patient's teeth when updated image is acquired at step b).

Preferably, a first optimization operation is done for each test of a reference model to test during the second optimization operation.

Step e) may particularly include the following steps:

e'1) defining the reference model to test as being the initial reference model then, e'2) following the next steps, testing virtual acquisition conditions with the reference model to test in order to finely approximate said actual acquisition conditions;

e'21) determining virtual acquisition conditions to test;

e'22) creating a two-dimensional reference image of the reference model to test under said virtual acquisition conditions to test;

e'23) processing the reference image to create at least one reference map representing said discriminant information;

e'24) comparing the updated and reference maps so as to determine a value for a first evaluation function, said value for the first evaluation function depending on the differences between said updated and reference maps and corresponding to a decision to continue or to stop the search for virtual acquisition conditions approximating said actual acquisition conditions with more accuracy than said virtual acquisition conditions to test determined at the last occurrence of step e'21);

e'25) if said value for the first evaluation function corresponds to a decision to continue the search, resumption at step e'21) by modifying the virtual acquisition conditions to test;

e'3) otherwise determining a value for a second evaluation function, said value for the second evaluation function depending on the differences between the updated and reference maps under the virtual acquisition conditions best approximating said actual acquisition conditions and resulting from the last occurrence of step e'2), said value for the second evaluation function corresponding to a decision to continue or stop the search for a reference model approximating the shape and optionally the positioning of the teeth during the acquisition of the updated image with more accuracy than said reference model to test used at the last occurrence of step e'2), and if said value for the second evaluation function corresponds to a decision to continue said search, modification of the reference model to test by deformation of one or more tooth models or of the reference model to test and optionally by movement of one or more tooth models, then resumption at step e'2).

At the end of this process, a reference model to test called "updated reference model" is obtained, which corresponds to the initial reference model deformed to best correspond to the updated image.

The comparison of the initial and updated reference models includes the comparison of the spatial coordinates of the points of the surfaces defined by these two reference models. One can therefore deduce any changes in shape between step a) and step b).

Figure 8:
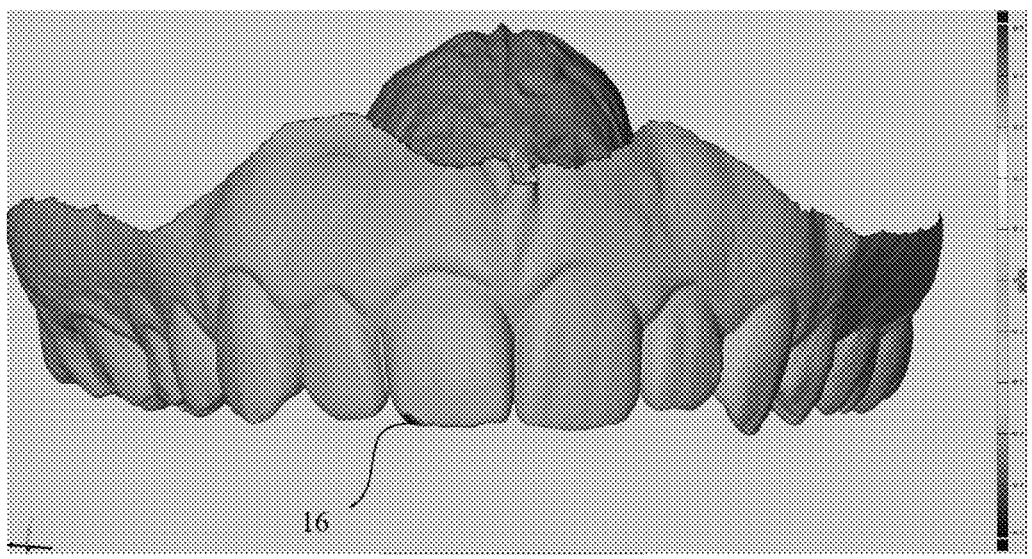
FIG. 8 is a map resulting from the implementation of a method for checking the shape of a patient's teeth according to the invention.

Preferably, a map of the tooth is produced showing the changes in shape. Preferably, as shown in FIG. 8, the color of an area of the map depends on the magnitude of shape change in this area. The map of FIG. 8 shows, in particular, an area 16 indicating a break in a tooth.

Of course, the method for checking the shape of a patient's teeth may be used to detect an addition or subtraction of material, as well as a deformation with constant volume. This method also permits detecting tooth movements, even without tooth models. However, in the absence of a tooth model, they do not permit distinguishing tooth deformations, on the one hand, and tooth movements, on the other hand.

Detailed Description of a Method for Checking the Appearance of the Teeth

Checking the evolution of the color of teeth from photographs taken from different positions of the camera or in different light environments shows that this comparison does not allow evaluation of an evolution of the appearance of these teeth.

Such a check of tooth color therefore requires special precautions, notably to precisely define the position of the camera and its light environment.

There is therefore a need for a method permitting checking the color, and more generally an appearance property, of teeth in the simplest way, and notably while avoiding these special precautions.

One objective of the invention is to meet this need.

Figure 9:
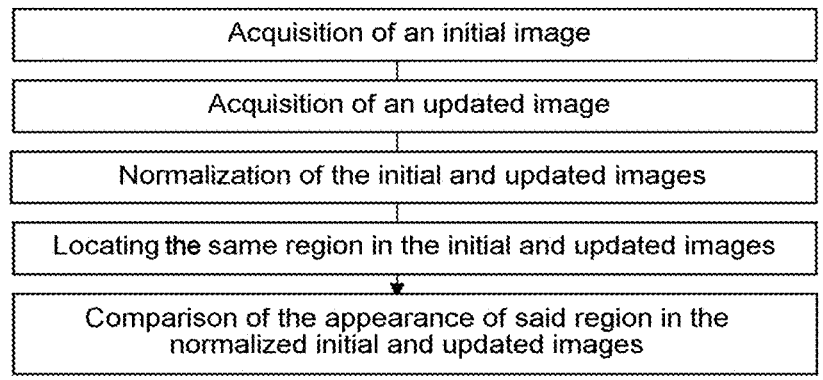
FIG. 9 is a flowchart illustrating the implementation of a method for checking the appearance of the teeth according to the invention.

The invention provides a method for checking an appearance property of a patient's teeth, said method including steps A. to E. described above, shown in FIG. 9.

As will be seen in more detail in the following description, this method makes it possible to evaluate whether the appearance, in particular the color of one or more of the teeth, has been modified, even when the acquisition conditions for the photographs of a patient's teeth are not predefined, for example because the photographs were taken in a bright environment or in any position of the acquisition device, particularly by the patient.

"Appearance property" means a property relating to appearance. The appearance property may be, in particular, chosen from the group made up of color, opalescence, fluorescence, gloss, transparency and combinations of these properties.

"Appearance" means a value or a collection of values to quantify an appearance property. Unless otherwise indicated, the "appearances" mentioned in this description concern the appearance property that the method allows to be checked.

Steps A. and B

Steps A. and B. may be conducted like step b) described above.

Steps A. and B. are preferably done by the patient or an associate of the patient, but may be done by a dentist.

The time interval between these steps may be the one described above between steps a) and b), for example more than 1 week, 2 weeks, 1 month, or 3 months.

The first acquisition device may be identical to or different from the second acquisition device. It may be an acquisition device chosen from among those that may be used for step b), notably a camera or a mobile phone.

Preferably, the acquisitions at steps A. and/or B. are done with a flash. The results are improved. Preferably, the initial image and/or the updated image is overexposed.

The reference gauges used for each of steps A. and B. have the same appearance. Preferably, during each of the steps, they are arranged in the same position relative to the patient's teeth.

Preferably, dental retractors are used for each of steps A. and B. These retractors may be identical or different. Preferably, the reference gauge is borne by a retractor for at least one of steps A. and B., preferably for each of steps A. and B. Preferably, even if the retractors used for each of the steps A. and B. are different, the reference gauges are arranged on the spacers in the same position relative to the opening 14 of the retractor which shows the teeth of the patient (FIG. 5*a*).

Preferably, the reference gauge is arranged on the retractor so as to be close to the teeth whose appearance property is to be checked. Preferably, the reference gauge is positioned less than 3 cm, preferably less than 2 cm, preferably less than 1 cm from the part of the retractor intended to be introduced into the patient's mouth.

Preferably, each retractor has several reference gauges, which are identical or different. Preferably, several different reference gauges of the same retractor have different appearances. The conclusions drawn from the comparison of the normalized images may advantageously be richer.

A reference gauge may be, for example, an identifiable point on the retractor and whose appearance is known, for example, whose color parameters $L^*$, and/or $a^*$ and/or $b^*$, measured according to standard NF ISO 7724, are known. The reference gauge may notably be an identification mark on a retractor such as described above.

The acquisition conditions specify the position in space and/or the orientation of the acquisition device relative to the retractor.

In order to improve the precision of the appearance checkup, it is preferable that the acquisition conditions be roughly the same at steps A. and B. For example, it is preferable that both images be taken essentially from the front. Preferably, the image acquisition device used for at least one, preferably each of steps A. and B. includes foolproofing means facilitating its positioning relative to the patient before the image is acquired.

The foolproofing means preferably interact with identification marks arranged on the retractor. Preferably, the acquisition device is programmed so as, in real time, to locate the identification marks on the retractor, analyze their relative positions or their dimensions and, accordingly, inform the user of the acquisition device so that they can accordingly change the position of the acquisition device relative to the patient's teeth.

These foolproofing means may have one or more of the characteristics of the foolproofing means described above for step b).

Preferably, for at least one, preferably each of steps A. and B., an acquisition kit according to the invention is used and, preferably, an acquisition method including steps (a) to (e). Preferably, the target acquisition conditions are the same in the memory of the first and second acquisition devices so that the acquisition device guides its user so that the initial and updated images are taken under essentially identical acquisition conditions.

Preferably, the target acquisition conditions are determined depending on the teeth for which the appearance property is to be checked. For example, the target acquisition conditions preferably correspond to taking an image from the front of the patient for checking an incisor and they preferably correspond to taking an image from the side for checking a molar.

Step C

Step C. consists of normalizing, i.e., "correcting" the initial image and/or the updated image so that, after correction, the representations of the reference gauge on these images have the same appearance. Since the reference gauge does not change appearance between steps A. and B., any differences in appearance presented by the representations of the teeth in the normalized initial and updated images therefore correspond to differences in the actual appearance of said teeth.

The reference gauge is first sought in the initial image and in the updated image. A simple image analysis is sufficient for this purpose.

Normalization can be done on the initial image only in order to modify the representation of the reference gauge so that its appearance is identical to that of the representation of said reference gauge on the updated image. Normalization can alternatively be done on the updated image only in order to modify the representation of the reference gauge so that its appearance is identical to that of the representation of said reference gauge on the initial image. Finally, normalization can be done on the updated image and on the initial image in order to modify the representations of the reference gauges so that their appearances are identical to that of a standard gauge.

The normalization of an image is a well-known technique in the field of image processing. White balance is an example of image normalization.

Step D

Before or after step C., it is suitable to identify, in each of the initial and updated images, a region of the teeth for which one wishes to evaluate the evolution of the appearance.

The use of identification marks or reference gauges is possible, but remains imprecise. Preferably, the initial and updated images are analyzed in order to represent a discriminant information, of the type described above, for example the tooth contour.

The analysis of the initial and updated images may include one or more characteristics of step c), notably relating to the nature of the discriminant information and the processing to determine the discriminant information. The discriminant information is preferably optimized using an optimization process including steps C1 to C3.

Discriminant information common to both the initial and updated images is sought.

The discriminant information common to both the initial and updated images may then serve as a reference frame to locate said region in these two images. For example, the contour of the gums may have a succession of "points" between the teeth. This contour depends on the teeth considered and may therefore serve as a reference frame.

In one improved embodiment, the initial and updated images are located with respect to a reference model, preferably made in accordance with step a) (initial reference model) or resulting from the implementation of a method for checking the shape and/or positioning of the teeth according to the invention (updated reference model).

This location may be done as described above to locate the updated image in the context of methods for checking the shape and/or positioning of the teeth. Unlike these methods, the modification of the initial reference model to arrive at the updated reference model is, however, optional.

To locate an image with respect to the reference model, it is sufficient to look for the virtual acquisition conditions under which the acquisition device acquired said image by observing said reference model. This search is preferably done using a metaheuristic method, such as described above.

For this search, preferably a method for evaluating the actual acquisition conditions according to the invention is used, described below. This method is preferably implemented for each of the initial and updated images using the reference model. It permits "projecting" these images onto the reference model and therefore locating a point of these images on the reference model.

A region of the teeth whose appearance evolution is to be evaluated may thus be identified with great precision on each of the initial and updated images.

Step E

It is thus possible to measure the appearances of said region in each of the initial and updated images and to compare them in order to detect and evaluate differences in the appearance property.

A method for checking the appearance of teeth according to the invention may be used for therapeutic or nontherapeutic purposes. It may in particular be used to:

detect and/or measure a change in tooth color or appearance and/or evolution in stains on the teeth, or detect and/or measure calcification of the teeth.

check the effect on the appearance of the teeth of a dietary habit or dietary hygiene or a treatment, for example a whitening treatment, or a product, especially a toothpaste, in particular for whitening teeth or for combating calcification or the appearance of stains.

For example, a method for checking the appearance of teeth according to the invention may be used to check the effects on the appearance of the teeth of chewing gum or drinking coffee or tea, or using tobacco or drugs, or brushing the teeth.

In one preferred embodiment, it is sufficient for the patient to regularly take photographs with their mobile phone to make updated images. Preferably, using an app loaded on this phone, it is then possible to compare the appearance of the teeth in these photographs.

In one embodiment, the app normalizes the photographs to make them comparable, then offers a dynamic view of the corrected photographs, for example in the form of a slide show or movie.

Detailed Description of a Method for Evaluating Actual Acquisition Conditions In particular for the implementation of a method for checking the shape, positioning and/or appearance of teeth according to the invention or for optimizing the quality of a discriminant information, the invention provides a method for evaluating, from a two-dimensional image of the dental arches of a patient, called "acquired image", the actual acquisition conditions (position of the acquisition device in space, orientation of this device, and, preferably, calibration of the acquisition device) of said acquired image, said method comprising the following steps:
  001) creating a numerical three-dimensional reference model of at least a part of a patient's arch, preferably one arch, preferably both arches of the patient;
  002) analyzing the image acquired and creating a map relating to a discriminant information, called "acquired map";
  003) searching for virtual acquisition conditions optimally approximating the actual acquisition conditions, preferably according to steps 01) to 05) below:
    01) optionally, determining rough virtual acquisition conditions approximating said actual acquisition conditions, preferably by analyzing the representation, in the acquired image, of a retractor used during the acquisition of the acquired image;
    02) determining virtual acquisition conditions to test;
    03) creating a two-dimensional reference image of the reference model observed under the virtual conditions to test;
    04) processing the reference image to create at least one reference map representing said discriminant information;
    05) comparing the acquired and reference maps so as to determine a value for an evaluation function, said value for the evaluation function depending on the differences between said acquired and reference maps and corresponding to a decision to continue or to stop the search for virtual acquisition conditions approximating the actual acquisition conditions with more accuracy than said virtual acquisition conditions to test;
    06) if said value for the evaluation function corresponds to a decision to continue said search, modification of said virtual acquisition conditions to test, then resuming at step 03);
    otherwise, evaluating the actual acquisition conditions by said virtual acquisition conditions to test.

Preferably, the actual acquisition conditions to evaluate comprise one or more of the following calibration parameters: aperture, exposure time, exposure time, focal length and sensitivity.

In the evaluation method, the virtual acquisition conditions to test at step 06) are preferably modified by means of a metaheuristic method, preferably evolutionary, preferably by simulated annealing, preferably by one of the metaheuristic methods mentioned previously.

An evaluation method according to the invention is preferably used each time it is necessary to evaluate the actual acquisition conditions for an image. This image, which may, in particular, be an updated image acquired during step b) or B., or an initial image acquired during step A., is called "acquired image".

The creation of the reference model at step 001) may include one or more of the characteristics, even optional ones, of step a).

The acquisition of the acquired image may include one or more of the characteristics, even optional ones, of step b). Preferably, it implements an acquisition kit according to the invention, and preferably an acquisition method according to the invention.

Step 01) of determining rough virtual acquisition conditions may include one or more of the characteristics, even optional ones, of step c).

Steps 02) to 06) may include one or more of the characteristics, even optional ones, of steps e21) to e25), respectively.

Detailed Description of a Method for Optimizing, a Discriminant Information

A method for optimizing or "selecting" a discriminant information according to the invention is intended to improve the reliability of an initial discriminant information extracted from a two-dimensional image of the patient's dental arches, or "acquired image", in particular an initial image from a step A. or an updated image from a step B. or b), acquired under actual acquisition conditions. "Optimization" of discriminant information is therefore a selection of discriminant information, according to an iterative process, so as to select from the image the most relevant discriminant information to better check the positioning and/or shape of the patient's teeth.

This process relies on a numerical three-dimensional reference model of at least a part of a patient's arch, in particular, an initial reference model of step a).

Figure 10:
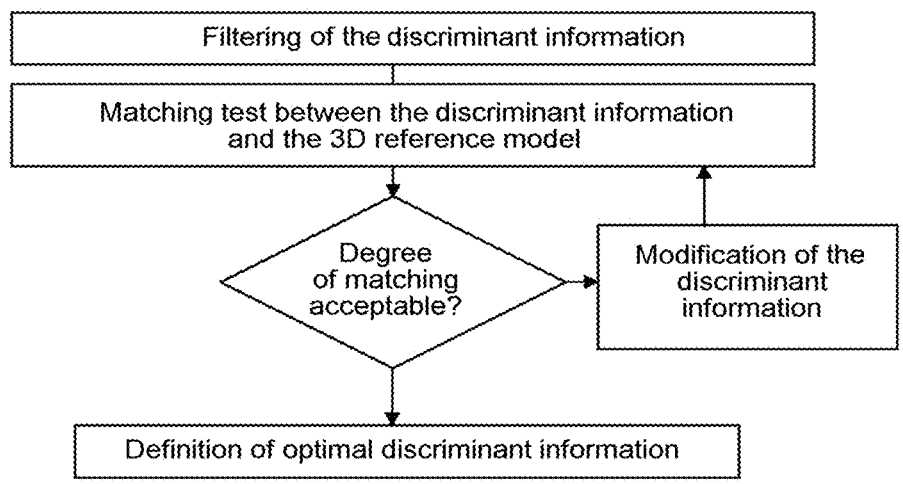
FIG. 10 is a flowchart illustrating the implementation of an optimization method for a discriminant information according to the invention.

As illustrated in FIG. 10, it includes the following steps:
  C1. evaluating the quality of the discriminant information and of a quality limit, filtering so as to retain only the initial discriminant information, preferably any initial discriminant information presenting a quality higher than the quality limit, and definition of "discriminant information to test" as being the discriminant information retained;
  C2. testing the match between the discriminant information to test and said reference model;
  C3. depending on the result and an evaluation function of the test result:

adding discriminant information not retained to the discriminant information to test and/or deletion of discrimination information in the discriminant information to test, then resumption at step C2. or, defining optimal discriminant information as being the discriminant information to test.

The discriminant information may notably be any of the discriminant information described previously. For example, the discriminant information may be contour information.

The initial discriminant information results conventionally from analysis of the acquired image, as described for step c).

The methods according to the invention that use such initial discriminant information implement optimizations that provide the best results if the discriminant information is both abundant and of good quality. One objective of the optimization method is therefore to improve the quality of the initial discriminant information.

At step C1., the quality of the initial discriminant information is evaluated. In the example of a contour, contrast analysis provides, for example, fairly reliable information: an area of high contrast may be equated to an area corresponding to a contour with a high probability and the quality of the points of this area will therefore be high. In contrast, an area of low contrast, for example a blurry area, may be equated to an area corresponding to a contour with a low probability and the quality of the points of this area will be therefore be low. In this example, the probability for a point of the acquired image to belong to the contour may be chosen as a "quality" indicator of the discriminant information.

A quality limit is used to filter the initial discriminant information. If the quality limit is high, the amount of discriminant information retained following the filtering will be small, but very reliable. If the quality limit is low, the amount of discriminant information retained will be high, but not very reliable. In the example of contour information, the analysis of the image will then lead to retaining "false" contour points, i.e., points which, because of the analysis, will be mistakenly considered to belong to the contour of the teeth and gums.

In one preferred embodiment, the quality limit is high in order to only retain very reliable discriminant information to test.

At step C2., the match is tested, i.e., a degree of matching is determined between the discriminant information to test and the reference model.

Preferably, an "acquired" map is made of the discriminant information to test resulting from processing the acquired image.

Preferably, one then proceeds to steps 01) to 06), and in particular the following steps:

02) determining virtual acquisition conditions to test;
03) creating a two-dimensional reference image of the reference model observed under the virtual acquisition conditions to test;
04) processing the reference image to create at least one reference map representing the discriminant information;
05) comparing the acquired and reference maps so as to determine a value for an evaluation function, said value for the evaluation function depending on the differences between said acquired and reference maps and corresponding to a decision to continue or to stop the search for virtual acquisition conditions approximating the actual acquisition conditions with more accuracy than said virtual acquisition conditions to test;
06) if said value for the evaluation function corresponds to a decision to continue said search, modification of said virtual acquisition conditions to test, then resumption at step 03);

otherwise, evaluating the actual acquisition conditions by said virtual acquisition conditions to test At step 04) processing the reference image allows a reference map representing said discriminant information to be created. The selection criteria for the discriminant information represented on the reference map may be identical or different from those used to select the discriminant information to test.

Preferably, the discriminant information shown on the reference map is selected with the same criteria as the discriminant information to test.

In the contour example, processing the reference image may consist of retaining the points of the reference image corresponding to a contour with a high probability.

The probably for a point of the reference image to belong to the contour may be determined as for the processing of the acquired image and also serve as an indicator of the quality of the discriminant information. The quality threshold may also be identical to the one used for processing the acquired image. The contour shown in the reference map is then similar to the one shown in the acquired map, and, in particular, has a roughly identical length.

Steps 01) to 06) permit determining, with the reference model, virtual acquisition conditions approximating the actual acquisition conditions for the acquired image.

The observation of the reference model under these virtual acquisition conditions therefore provides a view that best corresponds to the acquired image. The search for virtual acquisition conditions is based, however, on die discriminant information to test. The degree of correspondence therefore depends on the discriminant information to test. The higher the quality and quantity of the discriminant information to test, the better the degree of correspondence between the reference model view under the virtual acquisition conditions and the acquired image, and the higher the degree of matching between the discriminant information to test and the reference model.

The degree of matching may be, for example, measured by the inverse of the difference between the reference map relative to the reference model image observed under the virtual acquisition conditions best approximating the real acquisition conditions as a consequence of the execution of steps 01) to 06), and the "acquired" map representing the discriminant information to test corresponding to the acquired image weighted by the quantity of discriminant information to test.

For a contour, for example, the degree of matching can be the ratio of the number of points that belong to both the contour of the reference map and the contour of the acquired map, to the total number of points of the contour of the acquired map, or the product of the inverse of the mean distance between the contours represented on said acquired and reference maps, and the length of the contour represented on the acquired map.

The "best" approximation of the actual acquisition conditions from a discriminant information to test may be evaluated by a result or "score", for example by the degree of matching. The cycle of steps C2. and C3. aims to optimize this result by acting on the discriminant information to test.

This optimization is analogous to the one implemented for the methods for checking the positioning and/or the shape of the teeth. These methods, however, act on the initial reference model, by movement of the tooth models and/or by deformation of the reference model, whereas the optimization method for the discriminant information acts on the discriminant information used to establish the acquired map.

The operation done at step C3. is determined by a function of the evaluation of the result of step C2. Preferably, the evaluation function considers the results obtained during the preceding cycles C2.-C3.

In particular, the process may be stopped if the evaluation function indicates that continuing cycles C2.-C3. would not improve the result, for example, because one or more cycles C2.-C3. did not improve it or did not significantly improve it. The discriminant information tested during cycle C2.-C3. that led to the best result is then considered optimal.

Otherwise, a new cycle C2.-C3. may be launched, after modification of the discriminant information to test. The modification to make to the discriminant information that was just tested may consist of adding or removing discriminant information. It may be decided to add discriminant information, for example, if the latest result is the best one obtained so far and if, according to the evaluation function, the result may still be improved. Preferably, the discriminant information added is the one which, among the discriminant information not retained at step C1. and which has not yet been tested, presents the best quality.

For example, when the discriminant information is contour information, the addition of discriminant information may consist of adding image points not retained initially, never before added, and whose quality, as evaluated at step C1., is the highest, i.e., the addition of which is most likely to improve the test result of step C2.

It may be decided to remove discriminant information, for example, if the latest result is worse than the previous one. In particular, the discriminant information added during the preceding cycle may be removed and another discriminant information may be added, such as described previously.

The determination of the discriminant information to add and/or remove may be random. However, preferably, it results from the implementation of a metaheuristic method, preferably evolutionary, preferably by simulated annealing, preferably of the type of those described above.

Example

Figure 11:
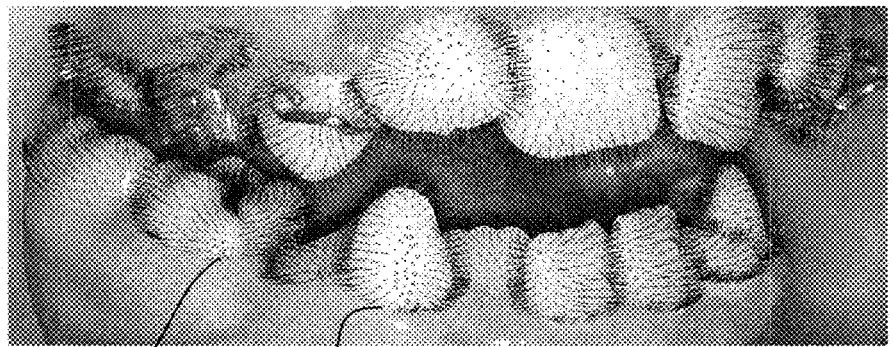
FIG. 11 is, in an acquired image, a reference map established for reflection information.

By way of example, FIG. 11 shows, superposed on the acquired image, a reference map relating to reflection information (discriminant information).

The acquired image, preferably acquired using an acquisition kit according to the invention, is a photograph taken in a particular position and orientation of the camera. This position and this orientation constitute the actual acquisition conditions for the acquired image.

The skilled person knows that, in the acquired image, the higher the brightness of a point, the greater the probability that this point belongs to a reflection area. Brightness may therefore serve as an indicator of the "quality" of reflection information.

The filtering at step C1. may consist of only retaining the areas of the acquired image that have a brightness greater than a quality threshold, for example of 70%.

The acquired map represents these areas, which constitute the discriminant information o test.

At step C2., one preferably proceeds according to steps 01) to 06) to test the retained areas match the observation of the reference model.

At step 01), the acquired image is analyzed to roughly evaluate the actual acquisition conditions by virtual acquisition conditions. This evaluation preferably results from an analysis of the position and/or the shape of the representation, in the acquired image, of identification marks of a retractor used during the acquisition.

The virtual acquisition conditions roughly evaluated may consist of "virtual acquisition conditions to test" at step 02).

At step 03), by observing the reference model from virtual acquisition conditions to test, a reference image is obtained.

At step 04), as shown in FIG. 11, vectors (black lines 20) may be projected onto the reference image, all of the same length, perpendicular to the faces of the reference model.

The circles 22 show these vectors when they are observed along their length. The reference map is thus made up of these black lines 20 and circles 22.

The skilled person knowns that circles 22 normally correspond to areas of the image corresponding to reflections. On the reference map, the discriminant information, i.e., the reflection information, is thus represented by black lines 20 and by circles 22, the inverse of the length of the black lines being able to serve as an indicator of the "quality" of the reflection information on the reference map, a circle corresponding to zero length, and therefore to a maximum quality.

At step 05), a comparison of the acquired and reference maps may consist, for example, of checking whether the lines 20 and the circles 22 are inside areas of the acquired map (which initially correspond to a brightness greater than 70%). The evaluation function may be, for example, the ratio R between
- the difference between the number of circles 22 and the number of lines that are inside the areas of the acquired image and
- the total number of circles 22.

The decision may be to continue the search by modifying the virtual acquisition conditions to test until reaching a maximum for the acquisition function.

At step 06), if this maximum is considered to be attained, the loop of steps 03) to 06) is exited. Otherwise, a modification to be made to the virtual acquisition conditions to test is determined, preferably using a metaheuristic method, preferably evolutionary, and step 03) is resumed.

On leaving steps 03) to 06), the ratio R is therefore maximum, for this acquired image, for example 95%. This ratio R then represents the result of the matching test done at step C2.

At step C3, this result is evaluated by means of an evaluation function.

This evaluation function preferably determines whether the result is optimal. If the result is considered optimal, for example because no better result could be attained after several cycles of steps C2.-C3., it is considered that the corresponding areas of the acquired map constitute an optimal discriminant information.

Otherwise, the acquired map is modified, for example by adding points of the acquired image, for example by adding points that have a brightness above 71%. This addition leads to the addition of circles in the areas of the acquired map, which improves the ratio R, but also to the addition of black lines, which degrades the ratio R. Conversely, it is possible to extract the points with a brightness greater than 69%. This removal leads to the removal of circles in areas of the acquired map, which degrades the ratio R, as well as the removal of black lines, which improves the ratio R.

The modification to introduce is preferably guided by a metaheuristic method, preferably evolutionary.

From the new acquired map, which defines the discriminant information to test, the cycle is resumed at step C2.

The cycling of steps C2. and C3. may be continued until an optimal result is determined.

The discriminant information to test is then considered optimal.

As it is now clear, a method for optimizing a discriminant information according to the invention makes it possible to construct discriminant information of good quality and volume. In particular, it allows, starting from a partial initial contour, but of good quality, gradually building a more complete contour but still of good quality.

Of course, the invention is not limited to the embodiments described and shown above.

In particular, unless otherwise indicated, the optional characteristics described in the context of a step of a first method according to the invention are applicable in the context of a similar step or a step bearing the same reference of a second method according to the invention.

The method for checking the positioning and/or the shape of teeth may be implemented successively for each of the two arches or simultaneously for both arches. Moreover, for these methods, several different devices may be implemented. For example, the acquisition can be done by a mobile phone and the subsequent steps with a stationary computer.

Finally, the patient is not limited to a human being. In particular, a method for checking the positioning of teeth according to the invention can be used for another animal.

The invention claimed is:

1. A method for adjusting an orthodontic appliance worn by a patient, the method including the following steps:
   a') Creating a numerical three-dimensional reference model of at least a part of a patient's arch, or "initial reference model";
   b') before or after step a'), before or after step c'), but before step d'), creating a numerical three-dimensional reference model, called "objective reference model", corresponding to a predetermined positioning, at a time point of the treatment, of the teeth of said at least a part of said patient's arch;
   c') Acquiring at least one updated image with an image acquisition device, under actual acquisition conditions, and searching, by deformation of the initial reference model, for an updated reference model corresponding to the positioning of the teeth during the acquisition of the updated image;
   d') Determining, depending on the initial reference model and/or the objective reference model, a comparison model, the comparison model being the objective reference model or a model corresponding to an anticipated positioning of the teeth essentially for the time point of said acquisition,
   e') Comparing the updated reference model with the comparison model;
   f') creation of a replacement orthodontic appliance, by modification of the orthodontic appliance worn or by creation of a new orthodontic appliance, the replacement orthodontic appliance being configured according to the result of said comparison.

2. The method as claimed in claim 1, wherein step c'), includes the following steps:
   b) Acquiring at least one two-dimensional image of the patient's arches, called "updated image", under actual acquisition conditions;
   c) Analyzing each updated image and creating, for each updated image, an updated map relating to a discriminant information;
   e) Searching, for each updated image, for an updated reference model corresponding to the positioning of the teeth when the updated image is acquired, step e) including the following steps:
      e1) defining a reference model to test as being the initial reference model then,
      e2) following the next steps, testing virtual acquisition conditions with the reference model to test in order to approximate said actual acquisition conditions;
         e21) determining virtual acquisition conditions to test;
         e22) creating a two-dimensional reference image of the reference model to test under said virtual acquisition conditions to test;
         e23) processing the reference image to create at least one reference map representing, at least partially, said discriminant information;
         e24) comparing the updated and reference maps so as to determine a value for a first evaluation function, said value for the first evaluation function depending on the differences between said updated and reference maps and corresponding to a decision to continue or to stop the search for virtual acquisition conditions approximating said actual acquisition conditions with more accuracy than said virtual acquisition conditions to test determined at the last occurrence of step e21);
         e25) if said value for the first evaluation function corresponds to a decision to continue said search, modification of the virtual acquisition conditions to test, then resumption at step e22);
      e3) determining a value for a second evaluation function, said value for the second evaluation function depending on the differences between the updated and reference maps under the virtual acquisition conditions best approximating said actual acquisition conditions and resulting from the last occurrence of step e2), and
      depending on said value for the second evaluation function,
      either stop said search, or
      modification of the reference model to test by movement of one or more tooth models, then resumption at step e2) so as to search for a reference model approximating the positioning of the teeth during the acquisition of the updated image with more accuracy than said reference model to test used at the last occurrence of step e2).

3. The method as claimed in claim 1, wherein the comparison model provides an estimation of the positioning, planned for an intermediate time point, of the teeth of the initial reference model, the duration between said intermediate time point and the time point of the acquisition done at step c') being less than 1 month.

4. The method as claimed in claim 1, including more than 2checkup cycles, each cycle being made up of an execution of steps c') to f').

5. The method as claimed in claim 4, wherein, at step d'), the comparison model is determined according to the updated reference models determined during one or more steps c') of checkup cycles prior to the checkup cycle including said step d').

6. The method as claimed in claim 4, wherein at step c'), said updated image is acquired by means of the patient's telephone.

7. The method as claimed in claim 4, wherein at least one step c') is scheduled at a schedule date, and before each said scheduled date for a step c'), a reminder message is sent to the patient, on their telephone, so that they may do said step c').

8. The method as claimed in claim 1, wherein, at step d'), the comparison model is determined according to the parameter values of the orthodontic appliance worn.

9. The method as claimed in claim 1, wherein, at step e'), a report is established from said comparison providing diagnostic information and/or recommendations to modify the patient's treatment.

10. The method as claimed in claim 1, wherein, at step e'),
    a score is established from said comparison, called "updated score", representing the treatment efficacy, and,
    said updated score is compared to a reference score representing the efficacy of treatment and the patient is presented with the result of the comparison between the updated and reference scores.

11. The method as claimed in claim 1, wherein at an orthodontic archwire of the orthodontic appliance worn has a tension, and, at step f'), said tension is modified, and/or an orthodontic archwire of the orthodontic appliance worn is switched out and/or an orthodontic aligner is created to replace said orthodontic appliance worn.

12. The method as claimed in claim 1, wherein, at step f), a plurality of potential treatments for achieving a positioning of the teeth corresponding to the objective reference model is determined, said potential treatments are presented to the patient and/or to an orthodontist so that they may choose one of said potential treatments, and then said replacement orthodontic appliance corresponding to the chosen treatment is created.

13. The method as claimed in claim 1, wherein, at step f), a replacement aligner for the orthodontic appliance worn is created and said second aligner is sent to the patient.

14. The method as claimed in claim 2, wherein the discriminant information is chosen in the group made up of contour information, color information, density information, distance information, brightness information, saturation information, information regarding reflections and combinations of these pieces of information.

15. The method according to claim 1, wherein the image acquisition device is a telephone of the patient configured to do the search for the updated reference model and to transmit the updated reference model to an orthodontist, and wherein the new orthodontic appliance is an orthodontic aligner for replacing the orthodontic appliance worn.

16. The method according to claim 1, in which the objective reference model numerically represents, in three dimensions, the teeth to treat in a position to be achieved at the end of the treatment.

17. The method according to claim 1, in which, at step f), a series of replacement orthodontic appliances is created and sent to the orthodontist or the patient.

18. The method according to claim 1, in which the initial reference model is deformed to create the objective reference model.

19. The method according to claim 15, in which the initial reference model is deformed by moving teeth models.

20. The method as claimed in claim 2, wherein the search is done by means of a metaheuristic method.

21. The method according to claim 3, in which the duration between said intermediate time point and the time point of the acquisition done at step c') is less than 1 week.

22. The method according to claim 6, in which the updated reference model is sought using said telephone.

23. The method as claimed in claim 4, including more than 10 checkup cycles, each cycle being made up of an execution of steps c') to f').

24. The method according to claim 6, in which the updated reference model is transmitted via said telephone to an orthodontist.

25. A method for evaluating the behavior of an orthodontic appliance including
    implementing, in several iterations, an adjustment method as claimed in claim 1, with said orthodontic appliance and/or orthodontic appliances of the same type,
    for each occurrence of the adjustment method, implementing a data collection, said data including at least the initial reference model and/or the objective reference model, on the one hand, and one or more updated reference models, on the other hand, as well as parameter values of the orthodontic appliance worn by the patient during said occurrence,
    implementing a statistical analysis of said data so as to establish a correlation between a parameter of the orthodontic appliance or appliances worn during said occurrences and the behavior of the orthodontic appliance or appliances worn.

26. The method as claimed in claim 25, wherein said adaptation method is implemented more than 1000 times.

27. The method as claimed in claim 25, wherein, after said statistical analysis, the results of said statistical analysis are used to optimize:
    the design of an orthodontic appliance, and/or
    the choice of an orthodontic appliance for a particular treatment and/or
    the establishment of a diagnosis, and/or
    the creation of a replacement orthodontic appliance, and/or
    the determination of a predictive model to create the comparison model.

* * * * *